United States Patent
Addison et al.

(10) Patent No.: US 11,096,588 B2
(45) Date of Patent: Aug. 24, 2021

(54) SYSTEM AND METHOD FOR MONITORING AUTOREGULATION UTILIZING NORMALIZED REGIONAL OXYGEN SATURATION VALUES

(71) Applicant: COVIDIEN LP, Mansfield, MA (US)

(72) Inventors: Paul Stanley Addison, Edinburgh (GB); James N. Watson, Edinburgh (GB); Dean Montgomery, Edinburgh (GB)

(73) Assignee: Covidien LP, Manfield, MA (US)

( * ) Notice: Subject to any disclaimer, the term of this patent is extended or adjusted under 35 U.S.C. 154(b) by 880 days.

(21) Appl. No.: 15/285,634

(22) Filed: Oct. 5, 2016

(65) Prior Publication Data
US 2017/0095161 A1    Apr. 6, 2017

Related U.S. Application Data

(60) Provisional application No. 62/237,871, filed on Oct. 6, 2015.

(51) Int. Cl.
*A61B 5/0205* (2006.01)
*A61B 5/021* (2006.01)
(Continued)

(52) U.S. Cl.
CPC ........ *A61B 5/0205* (2013.01); *A61B 5/02125* (2013.01); *A61B 5/14553* (2013.01);
(Continued)

(58) Field of Classification Search
CPC .. A61B 5/0059; A61B 5/02028; A61B 5/0261
See application file for complete search history.

(56) References Cited

U.S. PATENT DOCUMENTS

| 4,776,339 A | 10/1988 | Schreiber |
| 5,351,685 A | 10/1994 | Potratz |

(Continued)

FOREIGN PATENT DOCUMENTS

| CN | 101454654 A | 6/2009 |
| CN | 102440786 A | 5/2012 |

(Continued)

OTHER PUBLICATIONS

International Search Report and Written Opinion for PCT Application No. PCT/US2016/055504 dated Dec. 23, 2016; 11 pgs.

(Continued)

*Primary Examiner* — Rajeev P Siripurapu
*Assistant Examiner* — Michael A Catina
(74) *Attorney, Agent, or Firm* — Shumaker & Sieffert, P.A.

(57) ABSTRACT

A method for monitoring autoregulation includes, using a processor, receiving a blood pressure signal an oxygen saturation signal, and a regional oxygen saturation signal from a patient. The method also includes normalizing the regional oxygen saturation signal to correct for variation in the oxygen saturation signal based on a relationship between the oxygen saturation signal and the regional oxygen saturation signal. The method further includes determining a linear correlation between the blood pressure signal and the normalized regional oxygen saturation signal. The method still further includes providing a signal indicative of the patient's autoregulation status to an output device based on the linear correlation.

20 Claims, 9 Drawing Sheets

(51) Int. Cl.
 *A61B 5/1455* (2006.01)
 *A61B 5/00* (2006.01)
 *A61B 5/022* (2006.01)

(52) U.S. Cl.
 CPC .......... *A61B 5/6814* (2013.01); *A61B 5/6826* (2013.01); *A61B 5/7246* (2013.01); *A61B 5/742* (2013.01); *A61B 5/7405* (2013.01); *A61B 5/746* (2013.01); *A61B 5/022* (2013.01); *A61B 5/02108* (2013.01)

(56) References Cited

U.S. PATENT DOCUMENTS

| | | | |
|---|---|---|---|
| 5,482,034 | A | 1/1996 | Lewis et al. |
| 5,533,507 | A | 7/1996 | Potratz |
| 5,577,500 | A | 11/1996 | Potratz |
| 5,584,296 | A | 12/1996 | Cui et al. |
| 5,626,140 | A | 5/1997 | Feldman et al. |
| 5,803,910 | A | 9/1998 | Potratz |
| 5,934,277 | A | 8/1999 | Mortz |
| 6,385,471 | B1 | 5/2002 | Mortz |
| 6,438,399 | B1 | 8/2002 | Kurth |
| 6,453,183 | B1 | 9/2002 | Walker |
| 6,505,060 | B1 | 1/2003 | Norris |
| 6,510,329 | B2 | 1/2003 | Heckel |
| 6,599,251 | B2 | 7/2003 | Chen et al. |
| 6,668,182 | B2 | 12/2003 | Hubelbank |
| 6,714,803 | B1 | 3/2004 | Mortz |
| 6,754,516 | B2 | 6/2004 | Mannheimer |
| 6,896,661 | B2 | 5/2005 | Dekker |
| 6,987,994 | B1 | 1/2006 | Mortz |
| 7,001,337 | B2 | 2/2006 | Dekker |
| 7,221,969 | B2 | 5/2007 | Stoddart et al. |
| 7,268,873 | B2 | 9/2007 | Sevick-Muraca et al. |
| 7,744,541 | B2 | 6/2010 | Baruch et al. |
| 8,369,914 | B2 | 2/2013 | Niwayama |
| 8,556,811 | B2 | 10/2013 | Brady |
| 8,571,622 | B2 | 10/2013 | Huiku et al. |
| 2004/0097797 | A1 | 5/2004 | Porges et al. |
| 2005/0004479 | A1 | 1/2005 | Townsend et al. |
| 2005/0033129 | A1 | 2/2005 | Edgar, Jr. et al. |
| 2005/0192488 | A1 | 9/2005 | Bryenton et al. |
| 2005/0192493 | A1 | 9/2005 | Wuori |
| 2007/0004977 | A1 | 1/2007 | Norris |
| 2007/0049812 | A1 | 3/2007 | Aoyagi et al. |
| 2008/0081974 | A1 | 4/2008 | Pav |
| 2008/0146901 | A1 | 6/2008 | Katura et al. |
| 2008/0200785 | A1 | 8/2008 | Fortin |
| 2008/0228053 | A1 | 9/2008 | Wang et al. |
| 2009/0209836 | A1* | 8/2009 | Niwayama ......... G01N 21/4795 600/324 |
| 2009/0326386 | A1 | 12/2009 | Sethi et al. |
| 2010/0010322 | A1 | 1/2010 | Brady |
| 2010/0030054 | A1 | 2/2010 | Baruch et al. |
| 2010/0049082 | A1 | 2/2010 | Hu et al. |
| 2011/0046459 | A1 | 2/2011 | Zhang et al. |
| 2011/0105912 | A1* | 5/2011 | Widman ............ A61B 5/02028 600/483 |
| 2012/0149994 | A1 | 6/2012 | Luczyk et al. |
| 2012/0253211 | A1 | 10/2012 | Brady et al. |
| 2012/0271130 | A1* | 10/2012 | Benni ................ A61B 5/14551 600/324 |
| 2013/0190632 | A1 | 7/2013 | Baruch et al. |
| 2014/0073888 | A1 | 3/2014 | Sethi et al. |
| 2014/0275818 | A1 | 9/2014 | Kassem et al. |
| 2014/0278285 | A1 | 9/2014 | Marmarelis et al. |
| 2016/0106372 | A1 | 4/2016 | Addison et al. |
| 2016/0324425 | A1 | 11/2016 | Addison et al. |
| 2016/0345913 | A1 | 12/2016 | Montgomery et al. |
| 2016/0367197 | A1 | 12/2016 | Addison et al. |
| 2017/0000395 | A1 | 1/2017 | Addison et al. |
| 2017/0000423 | A1 | 1/2017 | Addison et al. |
| 2017/0105631 | A1 | 4/2017 | Addison et al. |
| 2017/0105672 | A1 | 4/2017 | Addison et al. |

FOREIGN PATENT DOCUMENTS

| | | |
|---|---|---|
| EP | 615723 A1 | 9/1994 |
| WO | WO9843071 A1 | 10/1998 |
| WO | WO0059374 | 10/2000 |
| WO | WO03000125 A1 | 1/2003 |
| WO | WO03071928 A2 | 9/2003 |
| WO | WO2004075746 A2 | 9/2004 |
| WO | WO2008097411 A1 | 8/2008 |
| WO | WO2016182853 A1 | 11/2016 |

OTHER PUBLICATIONS

Eichhom, Lars, et al.: "Evaluation of newar-infrared spectroscopy under apnea-dependent hypoxia in humans", Journal of Clinical Monitoring and Computing, vol. 29, No. 6, Feb. 4, 2015, pp. 749-757.

Alexander Caicedo et al.: "Cerebral Tissue Oxygenation and Regional Oxygen Saturation Can be Used to study cerebral Autoregulation in Prematurely Born Infants," Pediatric Research, vol. 69, No. 6, Jun. 1, 2011, pp. 548-553.

International Search Report and Written Opinion from International Application No. PCT/US2016/055504, dated Dec. 23, 2016, 9 pp.

U.S. Appl. No. 15/666,167, filed Aug. 1, 2017, naming inventors Addison et al.

Chuan et al., "Is cerebrovascular autoregulation associated with outcomes after major noncardiac surgery? A prospective observational pilot study," Acta Anaesthesiol Scand., Aug. 5, 2018, 10 pp.

Addison, P. S., et al.; "Low-Oscillation Complex Wavelets," Journal of Sound and Vibration, 2002, vol. 254, Elsevier Science Ltd., pp. 1-30.

Addison, P. S.; "The Illustrated Wavelet Transform Handbook," 2002, IOP Publishing Ltd., Bristol, UK, Ch. 2.

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Barreto, Armando B., et al.; "Adaptive LMS Delay Measurement in dual Blood Volume Pulse Signals for Non-Invasive Monitoring," *IEEE*, pp. 117-120 (1997).

Bassan, Haim, et al.; "Identification of pressure passive cerebral perfusion and its mediators after infant cardiac surgery," Pediatric Research Foundation, vol. 57, No. 1, 2005; pp. 35-41.

Belal, Suliman Yousef, et al.; "A fuzzy system for detecting distorted plethysmogram pulses in neonates and paediatric patients," *Physiol. Meas.*, vol. 22, pp. 397-412 (2001).

Brady, Ken M., et al.; "Continuous Measurement of Autoregulation by Spontaneous Fluctuations in Cerebral Perfusion Pressure Comparison of 3 Methods," NIH Public Access Author Manuscript, Stroke, 2008, 39(9), pp. 1-13.

Brady, Ken M., et al.; "Continuous time-domain analysis of cerebrovascular autoregulation using near-infrared spectroscopy," American Stroke Association, DOI:10.1161/strokeaha.107.485706, Aug. 2007, pp. 2818-2825.

Brady, Ken M., et al.; "Monitoring cerebral blood flow pressure autoregulation in pediatric patients during cardiac surgery," Stroke 2010;41:1957-1962 (http://stroke.ahajournals.org/content/41/9/1957.full).

Brady, Ken M., et al.; "Noninvasive Autoregulation Monitoring with and without Intracranial Pressure in a Naive Piglet Brain," Neuroscience in Anesthesiology and Perioperative Medicine, 2010, vol. 111, No. 1, International Anesthesia Research Society, pp. 191-195.

Brady, Kenneth, et al.; "Real-Time Continuous Monitoring of Cerebral Blood Flow Autoregulation Using Near-Infrared Spectroscopy in Patients Undergoing Cardiopulmonary Bypass," Stroke, 2010, 41, American Heart Association, Inc., pp. 1951-1956.

Caicedo, Alexander, et al.; "Cerebral Tissue Oxygenation and Regional Oxygen Saturation Can be Used to study Cerebral Autoregulation in Prematurely Born Infants," Pediatric Research, vol. 69, No. 6, Jun. 1, 2011, pp. 548-553.

Caicedo, Alexander, et al.; "Detection of cerebral autoregulation by near-infrared spectroscopy in neonates: performance analysis of

(56) References Cited

OTHER PUBLICATIONS measurement methods," Journal of Biomedical Optics 17 (11) pp. 117003-1-117003-9 (Nov. 2012).
Chan, K.W., et al.; "17.3: Adaptive Reduction of Motion Artifact from Photoplethysmographic. Recordings using a Variable Step-Size LMS Filter," IEEE, pp. 1343-1346 (2002)+A10.
Chen, Li, et al.; "The role of pulse oximetry plethysmographic waveform monitoring as a marker of restoration of spontaneous circulation: a pilot study," Chin Crit Care Med, 2015, vol. 27, No. 3, pp. 203-208.
Chen, Liangyou, et al.; "IS respiration-induced variation in the photoplethysmogram associated with major hypovolemia in patients with actue tramatic injuries," Shock, vol. 34, No. 5, pp. 455-460 (2010).
Cheng, Ran, et al.; "Noninvasive optical evaluation of spontaneous low frequency oscillations in cerebral hemodynamics", Neuroimage, Academic Press, vol. 62, No. 3, May 24, 2012, pp. 1445-1454.
Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.
Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.
Cysewska-Sobusaik, Anna; "Metrological Problems With noninvasive Transillumination of Living Tissues," *Proceedings of SPIE*, vol. 4515, pp. 15-24 (2001).
Czosnyka, Marek, et al.; "Monitoring of cerebrovascular autoregulation: Facts, Myths, and Missing Links," Neurocrit Care (2009) 10:373-386.
Daubechies, Ingrid, et al.; "A Nonlinear Squeezing of the Continuous Wavelet Transform Based on Auditory Nerve Models," Princeton University, 1996, Acoustic Processing Department, NY, pp. iii, 1-17.
Daubechies, Ingrid, et al.; "Synchrosqueezed Wavelet Transforms: an Empirical Mode Decomposition-like Tool," Princeton University, 2010, Applied and Computational Harmonic Analysis, pp. 1-32.
Dias, Celeste, et al.; "Optimal Cerebral Perfusion Pressure Management at Bedside: A Single-Center Pilot Study," Neurocritical care, vol. 23, No. 1, Jan. 8, 2015; pp. 92-102; ISSN: 1541-6933.
East, Christine E., et al.; "Fetal Oxygen Saturation and Uterine Contractions During Labor," *American Journal of Perinatology*, vol. 15, No. 6, pp. 345-349 (Jun. 1998)
Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engie in Medicine and Biology Society*, vol. 20, No. 6, p. 3072-3075, 1998.
Eichhorn, Lars, et al.; "Evaluation of newar-infrared spectroscopy under apnea-dependent hypoxia in humans," Journal of Clinical Monitoring and Computing, vol. 29, No. 6, Feb. 4, 2015, pp. 749-757.
Gao, Yuanjuin, et al.; "Response of cerebral tissue oxygenation and arterial blood pressure to postural change assessed by wavelet phase coherence analysis", 2014 7th International conference on Biomedical Engineering and Informatics, IEEE, Oct. 14, 2014, pp. 373-377.
Ge, Z.; "Significance tests for the wavelet cross spectrum and wavelet linear coherence," Annales Geophysicae, 2008, 26, Copernicus Publications on behalf of European Geosciences Union, pp. 3819-3829.
Gesquiere, Michael J., et al., "Impact of withdrawal of 450 ML of blook on respiration-induced oscillations of the ear plethysmographic waveform," Journal of Clinical Monitoring and Computing (2007) 21:277-282.
Goldman, Julian M.; "Masimo Signal Extraction Pulse Oximetry," *Journal of Clinical Monitoring and Computing*, vol. 16, pp. 475-483 (2000).

Gommer, Erik D., et al.; "Dynamic cerebral autoregulation: different signal processing methods without influence on results and reproducibility"; Medical & Biological Engineering & Computer; vol. 48, No. 12, Nov. 4, 2010; pp. 1243-1250.
Hamilton, Patrick S., et al.; "Effect of Adaptive Motion-Artifact Reduction on QRS Detection," *Biomedical Instrumentation & Technology*, pp. 197-202 (May-Jun. 2000).
Huang, J., et al.; "Low Power Motion Tolerant Pulse Oximetry," Anesthesia & Analgesia 2002 94: S103.
Johansson, A.; "Neural network for photoplethysmographic respiratory rate monitoring," *Medical & Biological Engineering & Computing*, vol. 41, pp. 242-248 (2003).
Kaestle, S.; "Determining Artefact Sensitivity of New Pulse Oximeters in Laboratory Using Signals Obtained from Patient," *Biomedizinische Technik*, vol. 45 (2000).
Kim, J.M., et al.; "Signal Processing Using Fourier & Wavelet Transform for pulse oximetry," pp. II-310-II-311 (2001).
Kirkham, S.K., et al.; "A new mathematical model of dynamic cerebral autoregulation based on a flow dependent feedback mechanism; Dynamic cerebral autoregulation modelling," Physiological Measurement, Institute of Physics Publishing, vol. 22, No. 3, Aug. 1, 2001; (13 pgs.).
Leahy, Martin J., et al.; "Sensor Validation in Biomedical Applications," *IFAC Modelling and Control in Biomedical Systems*, Warwick, UK; pp. 221-226 (1997).
Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.
Lee, Jennifer K., et al.; A pilot study of cerebrovascular reactivity autoregulation after pediatric cardiac arrest, Resuscitation 85, 2014, Elsevier Ireland Ltd., pp. 1387-1393.
Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).
Massart, Desire L., et al.; "Least Median of Squares: A Robust Method for Outlier and Model Error Detection in Regression and Calibration," Analytica Chimica Acta, 1986, Elsevier Science Publishers B.V., The Netherlands, pp. 171-179.
McGrath, S.P., et al.; "Pulse oximeter plethysmographic waveform changes in awake, spontaneously breathing, hypovolemic volunteers," Anesth. Analg. vol. 112 No. 2, pp. 368-374 (2010).
Montgomery, Dean, et al.; "Data cluestering methods for the determination of cerebral autoregulation functionality," Journal of Clinical Monitoring and Computing, vol. 30, No. 5, Sep. 16, 2015, pp. 661-668.
Morren, G., et al.; "Detection of autoregulation in the brain of premature infants using a novel subspace-based technique," 23rd Annual International Conference of IEEE Engineering in Medicine and Biology Society, Oct. 2001; pp. 1-4.
Morren, Geert, et al.; "Quantitation of the concordance between cerebral intravascular oxygenation and mean arterial blood pressure for the detection of impaired autoregulation," 29th Annual Meeting of the International Society on Oxygen Transport to Tissue, UofP, Aug. 2001; pp. 1-5.
Neumann, R., et al.; "Fourier Artifact suppression Technology Provides Reliable $SpO_2$," Anesthesia & Analgesia 2002, 94: S105.
Obrig, Hellmuth, et al.; "Spontaneous low frequency oscillations of cerebral heodynamics and metabolism in human adults," NeuroImage 12, 623-639 (2000).
Odagiri, Y.; "Pulse Wave Measuring Device," *Micromechatronics*, vol. 42, No. 3, pp. 6-11 (published Sep. 1998) (Article in Japanese—contains English summary of article).
Ono, Masahiro, et al.; "Validation of a stand-alone near-infrared spectroscopy system for monitoring cerebral autoregulaiton during cardiac surgery," International Anethesia Research Society, Jan. 2013, vol. 116, No. 1, pp. 198-204.
Panerai, B.; "Cerebral Autoregulation: from models to clinical Applications," Cardiovascular Engineering: an International Journal, vol. 8, No. 1, Nov. 28, 2007, (28 pgs.).

(56) References Cited

OTHER PUBLICATIONS

Payne, Stephen J., et al.; "Tissue Oxygenation Index as a Measure of Cerebral Autoregulation," Biomedial Engineering, Feb. 2004, Innsbruck, Austria, pp. 546-550.

Reinhard, Matthias, et al.; "Spatial mapping of dynamic cerebral autoregulation by multichannel near-infrared spectrosccopy in high-grade carotid artery disease", International Society for optical Engineering, SPIE, vol. 19, No. 9, Sep. 1, 2014, p. 97005.

Reinhard, Matthias, et al.; "Oscillatory cerebral hemodynamics—the macro- vs. microvascular level," Journal of the Neurological Sciences 250 (2006) 103-109.

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Rowley, A.B., et al.; "Synchronization between arterial blood pressure and cerebral oxyhaemoglobin concentration investigated by wavelet cross-correlation," Physiol. Meas., vol. 28, No. 2, Feb. 2007, pp. 161-173.

Shamir, M., et al.; "Pulse oximetry plethysmographic waveform during changes in blood volume," British Journal of Anaesthesia 82(2): 178-81 (1999).

Sorensen, Henrik, et al.; "A note on arterial to venous oxygen saturation as reference for NIRS-determined frontal lobe oxygen saturation in healthy humans," Frontiers in Physiology, vol. 4, Art. 403, Jan. 2014, pp. 1-3.

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Such, Hans Olaf; "Optoelectronic Non-invasive Vascular Diagnostics Using multiple Wavelength and Imaging Approach," *Dissertation*, (1998).

Todd, Bryan, et al.; "The Identification of Peaks in Physiological Signals," *Computers and Biomedical Research*, vol. 32, pp. 322-335 (1999).

Tsuji, Miles, et al.; "Cerebral intravascular oxygenation correlates with mean arterial pressure in critically ill premature infants," American Academy of Pediatrics, 2000; 106; pp. 625-632.

Wagner, Bendicht P., et al.; "Dynanic cerebral autoregulatory response to blood pressure rise measured by near-infrared spectroscopy and intracranial pressure," Critical Care Medicine 2002, vol. 30, No. 9, pp. 2014-2021.

Whitaker, E., et al.; "Cerebrovascular Autoregulation After Pediatric Cardiac Arrest," NEURO-85, 2012, 2 pgs.

Williams, Monica, et al.; "Intraoperative blood pressure and Cerebral perfusion: strategies to clarify hemodynamic goals," Paediatric Anaesthesia, vol. 24, No. 7, Jul. 12, 2014; pp. 657-667; XP055331904.

Wong, Flora Y., et al.; "Impaired Autoregulation in preterm infants identified by using spatially resolved spectroscopy," American Academy of Pediatrics DOI:10.1542 (2008) e604-611.

Wu, Dongmei, et al.; "Na*/H* Exchange inhibition delays the onset of hypovolemic circulatory shock in pigs," Shock, vol. 29, No. 4, pp. 519-525 (2008).

Wu, et al.; "Using synchrosqueezing transform to discover breathing dynamics from ECG signals," arXiv:1105.1571, vol. 2, Dec. 2013, pp. 1-9.

Wu, Hau-tieng, et al.; "Evaluating physiological dynamics via Synchrosqueezing: Prediction of Ventilator Weaning," Journal of Latex Class Files, vol. 11, No. 4, Dec. 2012, pp. 1-9.

Zhang, Rong, et al.; "Transfer function analysis of dynamic cerebral autoregulation in humans," 1998 the American Physiological Society; pp. H233-H241.

Zweifel, Christian, et al.; "Continuous time-domain monitoring of cerebral autoregulation in neurocritical care," Medical Engineering & Physics, Elsevier Ltd., vol. 36, No. 5, 2014, pp. 638-645.

U.S. Appl. No. 15/648,665, filed Jul. 13, 2017, Dean Montgomery.

Examination Report from counterpart European Application No. 16785609.5, dated Jul. 11, 2019, 4 pp.

International Preliminary Report on Patentability from International Application No. PCT/US2016/055504, dated Apr. 10, 2018, 6 pp.

Response to Examination Report from counterpart European Application No. 16785609.5, dated Dec. 23, 2019, 21 pp.

First Office Action, and machine translation, from counterpart Chinese Application No. 201680058021.6, dated Mar. 31, 2020, 22 pp.

Second Office Action and Search Report, and translation thereof, from counterpart Chinese Application No. 201680058021.6, dated Sep. 17, 2020, 11 pp.

\* cited by examiner

SYSTEM AND METHOD FOR MONITORING AUTOREGULATION UTILIZING NORMALIZED REGIONAL OXYGEN SATURATION VALUES

BACKGROUND

The present disclosure relates generally to medical devices and, more particularly, to systems and methods for monitoring autoregulation.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, medical professionals often desire to monitor certain physiological parameters of their patients. In some cases, clinicians may wish to monitor a patient's autoregulation. Autoregulation is a physiological process that attempts to maintain an optimal cerebral blood flow to supply appropriate levels of oxygen and nutrients to the brain. During autoregulation, cerebral arterioles dilate or constrict to maintain optimal blood flow. For example, as cerebral pressure decreases, cerebral arterioles dilate in an attempt to maintain blood flow. As cerebral pressure increases, cerebral arterioles constrict to reduce the blood flow that could cause injury to the brain. If the patient's autoregulation process is not functioning properly, the patient may experience inappropriate cerebral blood flow, which may have negative effects on the patient's health. In particular, a drop in cerebral blood flow may cause ischemia, which may result in tissue damage or death of brain cells. An increase in cerebral blood flow may cause hyperemia, which may result in swelling of the brain or edema.

Some existing systems for monitoring autoregulation may determine a patient's autoregulation status based on various physiological signals. Such physiological signals may be subject to variation due to various sources. One of these sources may be other physiological signals. However, existing systems for monitoring autoregulation may not account for variations in a physiological signal due to another physiological signal in determining the patient's autoregulation status. Accordingly, the autoregulation status determined by such existing systems may be inaccurate or unreliable.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A physician may monitor a patient's autoregulation through the use of various monitoring devices and systems. In accordance with the present disclosure, a patient's autoregulation may be monitored by correlating measurements of the patient's blood pressure (e.g., arterial blood pressure) with measurements of the patient's regional oxygen saturation. In particular, the patient's regional oxygen saturation may be normalized based on the relationship between oxygen saturation and regional oxygen saturation. This relationship may be based on historical data between oxygen saturation and regional oxygen saturation or based on the patient's measured oxygen saturation and regional oxygen saturation. For example, in the latter case, a curve based on the measured oxygen saturation and the regional oxygen saturation may be generated, a line of best fit applied to the curve, and a gradient (e.g., slope) of the line extracted. The gradient of the line may be utilized by the disclosed systems and methods to normalize the regional oxygen saturation. In particular, a cerebral oximetry index (COx) may be derived based at least in part on a linear correlation between the patient's blood pressure and normalized regional oxygen saturation. Normalizing the regional oxygen saturation may remove the variation in regional oxygen saturation due to changes in oxygen saturation. Also, the system and method enable more accurate autoregulation information to be presented to a medical professional, as discussed in more detail below.

Figure 1:
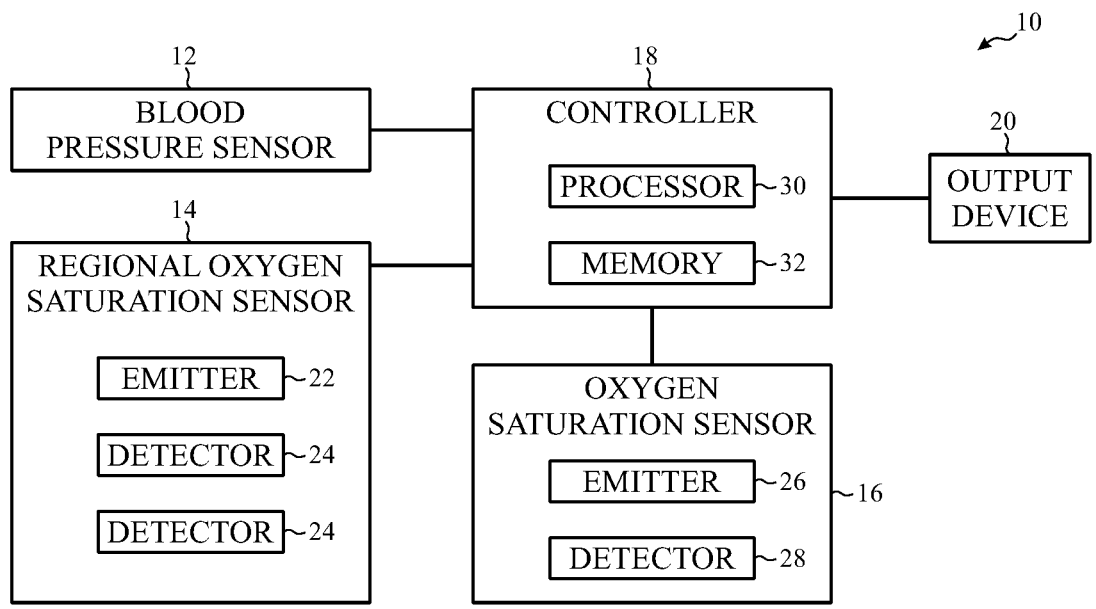
FIG. 1 is a block diagram of an embodiment of a system for monitoring a patient's autoregulation.

FIG. 1 illustrates an embodiment of a system 10 for monitoring autoregulation, in accordance with the present disclosure. As shown, the system 10 includes a blood pressure sensor 12, a regional oxygen saturation sensor 14, an oxygen saturation sensor 16, a controller 18, and an output device 20. The blood pressure sensor 12 may be any sensor or device configured to obtain the patient's blood pressure (e.g., arterial blood pressure). For example, the blood pressure sensor 12 may include a blood pressure cuff for non-invasively monitoring blood pressure or an arterial line for invasively monitoring blood pressure. In certain embodiments, the blood pressure sensor 12 may include one or more pulse oximetry sensors. In some such cases, the patient's blood pressure may be derived by processing time delays between two or more characteristic points within a single plethysmography (PPG) signal obtained from a single pulse oximetry sensor. Various techniques for deriving blood pressure based on a comparison of time delays between certain components of a single PPG signal obtained from a single pulse oximetry sensor are described in U.S. Publication No. 2009/0326386, entitled "Systems and Methods for Non-Invasive Blood Pressure Monitoring," the entirety of which is incorporated herein by reference. In other cases, the patient's blood pressure may be continuously, non-invasively monitored via multiple pulse oximetry sensors placed at multiple locations on the patient's body. As described in U.S. Pat. No. 6,599,251, entitled "Continuous Non-invasive Blood Pressure Monitoring Method and Apparatus," the entirety of which is incorporated herein by reference, multiple PPG signals may be obtained from the multiple pulse oximetry sensors, and the PPG signals may be compared against one another to estimate the patient's blood pressure. Regardless of its form, the blood pressure sensor 12 may be configured to generate a blood pressure signal indicative of the patient's blood pressure (e.g., arterial blood pressure) over time. As discussed in more detail below, the blood pressure sensor 12 may provide the blood pressure signal to the controller 18 or to any other suitable processing device to enable evaluation of the patient's autoregulation status.

The regional oxygen saturation sensor 14 may be configured to generate a regional oxygen saturation signal indicative of blood oxygen saturation within the venous, arterial, and capillary systems within a region of the patient. For example, the regional oxygen saturation sensor 14 may be configured to be placed on the patient's forehead and may be used to calculate the oxygen saturation of the patient's blood within the venous, arterial, and capillary systems of a region underlying the patient's forehead (e.g., in the cerebral cortex).

In such cases, the regional oxygen saturation sensor 14 may include an emitter 22 and multiple detectors 24. The emitter 22 may include at least two light emitting diodes (LEDs), each configured to emit at different wavelengths of light, e.g., red or near infrared light. In one embodiment, the LEDs of the emitter 22 emit light in the range of about 600 nm to about 1000 nm. In a particular embodiment, one LED of the emitter 22 is configured to emit light at about 730 nm and the other LED of the emitter 22 is configured to emit light at about 810 nm. One of the detectors 24 is positioned relatively "close" (e.g., proximal) to the emitter 22 and one of the detectors 24 is positioned relatively "far" (e.g., distal) from the emitter 22. Light intensity of multiple wavelengths may be received at both the "close" and the "far" detectors 24. For example, if two wavelengths are used, the two wavelengths may be contrasted at each location and the resulting signals may be contrasted to arrive at a regional saturation value that pertains to additional tissue through which the light received at the "far" detector passed (tissue in addition to the tissue through which the light received by the "close" detector passed, e.g., the brain tissue), when it was transmitted through a region of a patient (e.g., a patient's cranium). Surface data from the skin and skull may be subtracted out, to generate a regional oxygen saturation ($rSO_2$) signal for the target tissues over time. As discussed in more detail below, the regional oxygen saturation sensor 14 may provide the regional oxygen saturation signal to the controller 18 or to any other suitable processing device to enable evaluation of the patient's autoregulation status.

The oxygen saturation sensor 16 may be configured to generate an oxygen saturation signal indicative of blood oxygen saturation within the pulsatile tissue of the patient. For example, the oxygen saturation sensor 16 may be configured to be placed on the patient's finger and may be used to calculate the oxygen saturation of the patient's blood within the pulsatile tissue of the patient's finger.

In such cases, the oxygen saturation sensor 14 may include an emitter 26 and a detector 28. The emitter 26 may include at least two light emitting diodes (LEDs), each configured to emit at different wavelengths of light, e.g., red or near infrared light. In one embodiment, the LEDs of the emitter 26 emit light in the range of about 600 nm to about 1000 nm. In a particular embodiment, one LED of the emitter 26 is configured to emit light at about 730 nm and the other LED of the emitter 26 is configured to emit light at about 810 nm. In one embodiment, light enters the detector 28 after passing through the tissue of the patient. In another embodiment, light emitted from the emitter 26 may be reflected by elements in the patent's tissue to enter the detector 28. The detector 28 may convert the received light at a given intensity, which may be directly related to the absorbance and/or reflectance of light in the tissue of the patient, into an electrical signal (e.g., oxygen saturation ($SpO_2$) signal). As discussed in more detail below, the oxygen saturation sensor 16 may provide the oxygen saturation signal to the controller 18 or to any other suitable processing device to enable evaluation of the patient's autoregulation status.

In operation, the blood pressure sensor 12, the regional oxygen saturation sensor 14, and the oxygen saturation sensor 16 may each be placed on the same or different parts of the patient's body. Indeed, the blood pressure sensor 12, the regional oxygen saturation sensor 14, and/or the oxygen saturation sensor 16 may in some cases be part of the same sensor or supported by a single sensor housing. For example, the blood pressure sensor 12, the regional oxygen saturation sensor 14, and/or the oxygen saturation sensor 16 may be part of an integrated oximetry system configured to non-invasively measure blood pressure (e.g., based on time delays in a PPG signal) and oxygen saturation or regional oxygen saturation. One or more of the blood pressure sensor 12, the regional oxygen saturation sensor 14, and the oxygen saturation sensor 16 may be further configured to measure other parameters, such as hemoglobin, respiratory rate, respiratory effort, heart rate, saturation pattern detection, Bispectral™ index (BIS) or electromyography (EMG) response to electrical stimulus, or the like. While an exemplary system 10 is shown, the exemplary components illustrated in FIG. 1 are not intended to be limiting. Indeed, additional or alternative components and/or implementations may be used.

As noted above, the blood pressure sensor 12 may be configured to provide the blood pressure signal to the controller 18, the regional oxygen saturation sensor 14 may be configured to provide the regional oxygen saturation signal to the controller 18, and the oxygen saturation sensor 16 may be configured to provide the oxygen saturation signal to the controller 18. In certain embodiments, the controller 18 is an electronic controller having electrical circuitry configured to process the various received signals. In particular, the controller 18 may be configured to normalize the regional oxygen saturation signal based on the relationship with oxygen saturation to remove variation in the regional oxygen saturation due to changes in oxygen saturation. For example, with regard to the relationship, the controller 18 may utilize historical data (e.g., from the patient or other subjects) in normalizing the regional oxygen saturation signal. Alternatively, with regard to the relationship, the controller 18 may utilize both the oxygen saturation signal and the regional oxygen saturation signal in normalizing the regional oxygen saturation signal. For example, the controller 18 may construct a curve based on the oxygen saturation signal and the regional oxygen saturation signal, apply a best fit line to the curve, extract a gradient (e.g., slope) of the line, and utilize the gradient of the line in normalizing the regional oxygen saturation signal. In certain embodiments, the controller 18 may initially rely on the historical data in determining the relationship and, subsequently, switch to utilizing patient's data (i.e., derived from the oxygen saturation signal and the regional oxygen saturation signal) upon collecting sufficient patient data (i.e., enough data to calculate a reliable normalization gradient).

In some embodiments, the controller 18 may account for time delays in recording changes in $SpO_2$ at the finger when compared to measured $rSO_2$ at the forehead. In particular, the controller 18 may account for the time delay in normalizing the regional oxygen saturation signal.

In certain embodiments, the controller 18 may only apply normalization to the regional oxygen saturation signal if there is a strong correlation between $rSO_2$ and $SpO_2$. For example, the controller 18 may determine a quality metric (e.g., normalization quality metric), such as correlation coefficient or a significance value (e.g., p-value), compare it to a threshold, and normalize the regional oxygen saturation signal if the quality metric meets the threshold. In other embodiments, the controller 18 may only apply normalization to the regional oxygen saturation signal if $SpO_2$ falls below a particular threshold (e.g., 95% $SpO_2$).

Additionally, the controller 18 may be configured to process the blood pressure signal and the normalized regional oxygen saturation signal to evaluate the patient's cerebral autoregulation status. Although the blood pressure sensor 12, the regional oxygen saturation sensor 14, and/or the oxygen saturation sensor 16 may be configured to provide their respective signals or data directly to the controller 18, in certain embodiments, the signals or data obtained by the blood pressure sensor 12, the regional oxygen saturation sensor 14, and/or the oxygen saturation sensor 16 may be provided to one or more intermediate processing devices (e.g., specialized monitor, such as a blood pressure monitor or an oxygen saturation monitor, or the like), which may in turn provide processed signals or data to the controller 18.

As discussed in more detail below, the controller 18 may be configured to determine a cerebral oximetry index (COx) based on the blood pressure signal and the normalized regional oxygen saturation signal. The COx is indicative of vascular reactivity, which is related to cerebral blood vessels' ability to control proper blood flow, via vasoconstriction (a narrowing of the blood vessel) and/or vasodilation (expansion of the blood vessel), for example. Thus, the COx is also indicative of whether the patient's autoregulation is impaired. The controller 18 may derive the COx by determining a linear correlation between blood pressure measurements and the normalized oxygen saturation measurements. The linear correlation may be based on a Pearson coefficient, for example. The Pearson coefficient may be defined as the covariance of the measured blood pressure (e.g., arterial blood pressure or mean arterial blood pressure) and normalized regional oxygen saturation divided by the product of their standard deviations. The result of the linear correlation may be a regression line between normalized regional oxygen saturation measurements and blood pressure measurements, and the slope of the regression line may be indicative of the patient's autoregulation status. In one possible implementation, a regression line with a relatively flat or negative slope (e.g., blood pressure increases after regional oxygen saturation decreases) may suggest that cerebral autoregulation is working properly, while a regression line with a positive slope (e.g., blood pressure remains the same or decreases after regional oxygen saturation decreases) may suggest that the cerebral autoregulation is impaired.

The controller 18 may determine a value of the COx, which may be between −1 and 1, inclusive, where −1 represents total negative correlation, +1 represents total positive correlation, and 0 represents the absence of correlation between the blood pressure measurements and the normalized regional oxygen saturation measurements. Thus, COx values between −1 and 0 may suggest that cerebral autoregulation is working properly (i.e., intact), while COx values between 0 and 1 may suggest that the cerebral autoregulation is impaired. In some cases, a predetermined threshold between 0 and 1 may be utilized to determine whether the patient's autoregulation is impaired. For example, in some embodiments, the controller 18 may be configured to determine that the patient's autoregulation is impaired when the COx value is greater than 0.1, 0.2, 0.3, 0.4, 0.5, 0.6, 0.7, 0.8, or 0.9. In addition, the controller 18 may generate a COx curve (e.g., plotting COx values versus mean arterial pressure (MAP)) based on the COx values. Accordingly, the controller 18 may be configured to determine the COx value and/or the patient's autoregulation status based on the linear correlation between the blood pressure measurements and normalized regional oxygen saturation measurements obtained by the blood pressure sensor 12 and the regional oxygen saturation sensor 14, respectively.

In addition, the controller 18 may identify autoregulation zones indicative of a patient's blood pressure dependent autoregulation status. A patient's autoregulation system may typically function well over a certain range of blood pressures. Accordingly, each patient typically exhibits at least three autoregulation zones: a lower impaired autoregulation zone associated with relatively low blood pressures at which the patient's autoregulation function is impaired, an intact autoregulation zone associated with intermediate blood pressures at which the patient's autoregulation system works properly, and an upper impaired autoregulation zone associated with relatively high blood pressures at which the patient's autoregulation function is impaired. For example, although the blood pressures at which the autoregulation system functions properly may vary by patient, a particular patient may exhibit a lower impaired autoregulation zone associated with relatively low blood pressures of less than approximately 60 mmHg at which the patient's autoregulation function is impaired, an intact autoregulation zone associated with intermediate blood pressures between approximately 60 and 150 mmHg at which the patient's autoregulation system works properly, and an upper impaired autoregulation zone associated with relatively high blood pressures above approximately 150 mmHg at which the patient's autoregulation function is impaired. The controller 18 may determine an upper limit of autoregulation (ULA) value and/or a lower limit of autoregulation (LLA) that approximately define an upper and a lower blood pressure (e.g., upper and lower MAP) boundary, respectively, within which autoregulation is generally intact and functioning properly. Likewise, blood pressures approximately above the ULA and/or approximately below the LLA may be associated with impaired autoregulation function. Utilizing normalized regional oxygen saturation values in determining the COx value and COx curve may enable a more accurate LLA and/or ULA to be determined from the COx curve.

In the illustrated embodiment, the controller 18 includes a processor 30 and a memory device 32. The controller 18 may also include one or more storage devices. The processor 30 may be used to execute software, such as software for carrying out any of the techniques disclosed herein, such as processing the blood pressure signal, regional oxygen saturation signal, and/or oxygen saturation signal, normalizing the regional oxygen saturation signal, determining quality metrics, comparing quality metrics to one or more thresholds for determining whether to apply normalization to the regional oxygen saturation signal, determining the COx value, determining a LLA and/or ULA, and so forth. Moreover, the processor 30 may include multiple microprocessors, one or more "general-purpose" microprocessors, one or more special-purpose microprocessors, and/or one or more application specific integrated circuits (ASICS), or some combination thereof. For example, the processor 30 may include one or more reduced instruction set (RISC) processors.

The memory device 32 may include a volatile memory, such as random access memory (RAM), and/or a nonvolatile memory, such as ROM. The memory device 32 may include one or more tangible, non-transitory, machine-readable media collectively storing instructions executable by the processor 30 to perform the methods and control actions described herein. Such machine-readable media can be any available media that can be accessed by the processor 30 or by any general purpose or special purpose computer or other machine with a processor. The memory device 32 may store a variety of information and may be used for various purposes. For example, the memory device 32 may store processor-executable instructions (e.g., firmware or software) for the processor 30 to execute, such as instructions for carrying out any of the techniques discloses herein, such as processing the blood pressure signal, regional oxygen saturation signal, and/or the oxygen saturation signal, normalizing the regional oxygen saturation signal, determining quality metrics, comparing quality metrics to one or more thresholds for determining whether to apply normalization to the regional oxygen saturation signals, determining the COx value, determining a LLA and/or ULA. The storage device(s) (e.g., nonvolatile storage) may include read-only memory (ROM), flash memory, a hard drive, or any other suitable optical, magnetic, or solid-state storage medium, or a combination thereof. The storage device(s) may store data (e.g., the blood pressure signal, the regional oxygen saturation signal, the oxygen saturation signal, the COx, historical data for use in normalization, etc.), predetermined thresholds (e.g., $SpO_2$ threshold for triggering normalization and/or quality metric threshold for triggering normalization), normalization algorithms, and any other suitable data.

As shown, the system 10 includes the output device 20. In some embodiments, the controller 18 may be configured to provide signals indicative of the patient's autoregulation status to the output device 20. As discussed in more detail below, the controller 18 may be configured to generate an alarm signal indicative of the patient's autoregulation status and to provide the alarm signal to the output device 20. The output device 20 may include any device configured to receive signals (e.g., the signal indicative of the patient's autoregulation status, the alarm signal, or the like) from the controller 18 and visually and/or audibly output information indicative of the patient's autoregulation status (e.g., the COx value, the COx signal, $rSO_2$ value (pre-normalization), $rSO_2$—N value (after normalization), an alarm, or the like). For instance, the output device 20 may include a display configured to provide a visual representation of the patient's autoregulation status and/or the alarm signal as determined by the controller 18. Additionally or alternatively, the output device 20 may include an audio device configured to provide sounds in accordance with the alarm signal, the patient's autoregulation status, or both. The output device 20 may be any suitable device for conveying such information, including a computer workstation, a server, a desktop, a notebook, a laptop, a handheld computer, a mobile device, or the like. In some embodiments, the controller 18 and the output device 20 may be part of the same device or supported within one housing (e.g., a computer or monitor).

Figure 2:
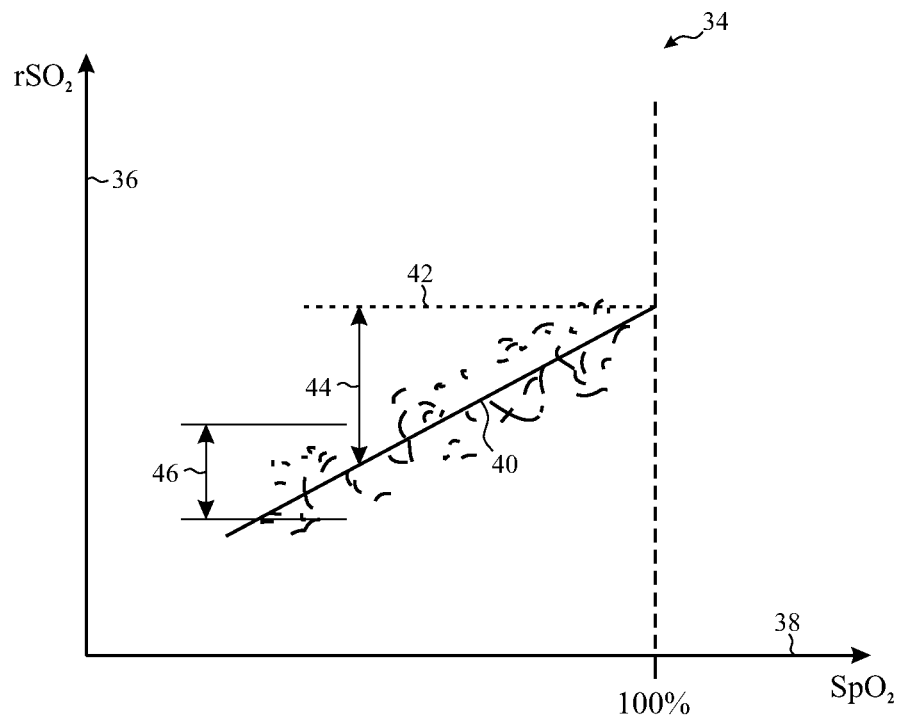
FIG. 2 is an example of a graph illustrating variation in regional oxygen saturation ($rSO_2$) due to changes in oxygen saturation ($SpO_2$) and other causes.

Variations in regional oxygen saturation may not occur solely due to changes in cerebral flow. FIG. 2 is an example of a graph 34 illustrating variation in regional oxygen saturation due to changes in oxygen saturation and other causes. The y-axis 36 represents regional oxygen saturation ($rSO_2$) and the x-axis 38 represents oxygen saturation ($SpO_2$). Besides changes in cerebral flow, changes in regional oxygen saturation may occur due to changes in oxygen saturation. The oxygen saturation-associated changes in regional oxygen saturation may affect the ability to correctly determine a correlation between regional oxygen saturation and blood pressure (e.g., to determine COx). Line 40 represents a line of best fit to the data. The line of best fit may be determined through least squares, least median squares, or other techniques. The line 40 illustrates the oxygen saturation-associated changes in regional oxygen saturation. Dashed line 42 illustrates the $rSO_2$ value in the absence of variation due to changes in $SpO_2$ (e.g., corresponding to $SpO_2$ value equaling 100%). Variation in $rSO_2$ due to changes in $SpO_2$ is illustrated by arrow 44. It is expected that as $SpO_2$ drops, $rSO_2$ should drop. However, variations in $rSO_2$ not associated with $SpO_2$ (represented by arrow 46) also take place and account for the depicted spread around the $rSO_2$—$SpO_2$ relationship. The spread may be due to other causes such as optical interference between the sensor and the tissue location, physical movement of the patient, and/or improper tissue-to-sensor positioning, for example.

Figure 3:
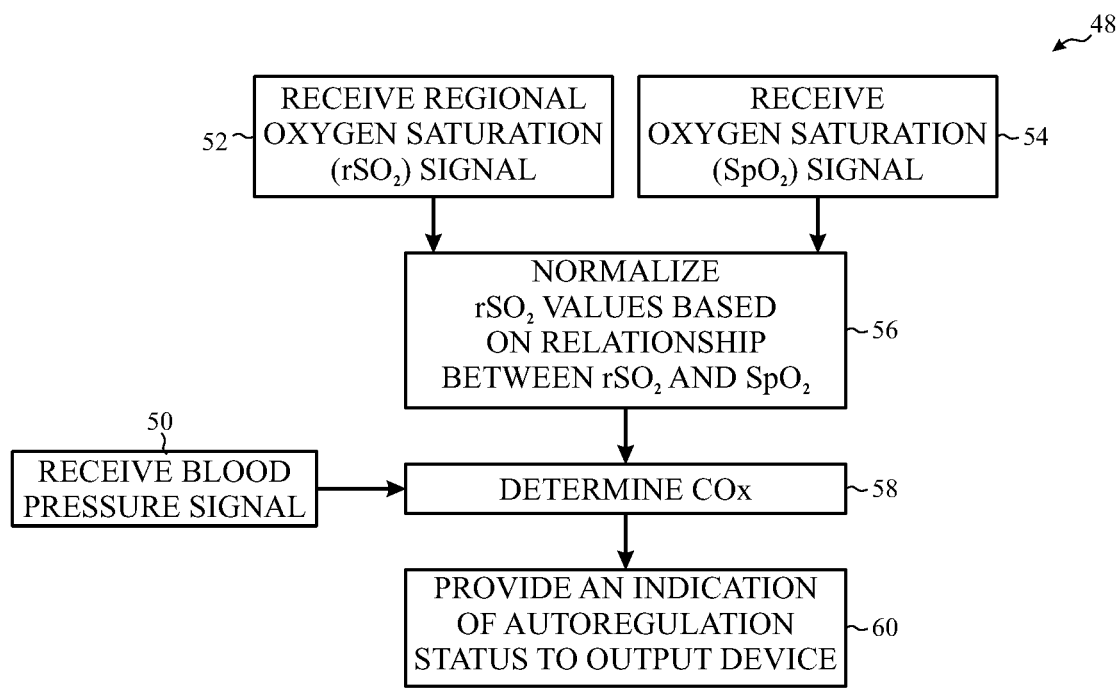
FIG. 3 is a process flow diagram of a method of monitoring autoregulation that includes normalizing a regional oxygen saturation signal, in accordance with an embodiment.

Normalizing the regional oxygen saturation based on its relationship with oxygen saturation may eliminate variation in the regional oxygen saturation due to changes in the oxygen saturation. FIG. 3 is a process flow diagram of a method 48 of monitoring autoregulation that includes normalizing a regional oxygen saturation signal, in accordance with an embodiment. Some or all of the steps of the method 48 may be implemented by the controller 18 (e.g., the processor 30 of the controller 18) of FIG. 1. In step 50, the controller 18 may receive the blood pressure signal (e.g., arterial blood pressure signal) from the blood pressure sensor 12, as set forth above. In step 52, the controller 18 may receive the regional oxygen saturation signal (e.g., from the regional oxygen saturation sensor 14, as set forth above). In step 54, the controller 18 may receive the oxygen saturation signal (e.g., from the oxygen saturation sensor 16, as set forth above). Steps 50, 52, and 54 may occur simultaneously.

In step 56, the controller 18 may normalize the regional oxygen saturation (i.e., $rSO_2$ values) signal (e.g., corresponding to a $SpO_2$ value equaling 100%) based on a relationship between regional oxygen saturation and oxygen saturation. In particular, in normalizing the regional oxygen saturation signal, the controller 18 may utilize the following equation:

$$rSO_2\text{—}N = rSO_2(i) + m \times (100 - SpO_2(i)), \quad (1)$$

wherein $rSO_2$—N represents the normalized $rSO_2$ value, $rSO_2$ (i) represents the currently acquired $rSO_2$ (i) value, $SpO_2$ (i) represents the currently acquired $SpO_2$ value, and m represents a numerical representation of the relationship between regional oxygen saturation and oxygen saturation ranging between 0 and 1. As discussed in greater detail below, m may be derived (e.g., precomputed) from historical data (e.g., of the patient or other subjects) or patient derived data (e.g., a gradient of a best fit line of an $rSO_2$—$SpO_2$ curve generated from the regional oxygen saturation signal and the oxygen saturation signal). In certain embodiments, m may be assumed to be 1.

In step 58, the controller 18 may determine the autoregulation status of the patient (e.g., COx) based on the linear correlation between blood pressure measurements of the blood pressure signal and the normalized regional oxygen saturation signal. In certain embodiments, the controller 18 may further determine the autoregulation status of the patient by plotting the COx value against the MAP (as well as determine the LLA and/or ULA) and determining whether the patient's autoregulation is intact or not (i.e., is the current blood pressure within an intact autoregulation zone). In step 60, the controller 18 may output the COx or a signal indicative of the patient's autoregulation status to the output device 20. In such cases, the controller 18 may cause the output device 20 to present a visual or audible indication of the COx value or the patient's autoregulation status. Also, the controller 18 may cause the output device 20 to provide a visual or audible indication of the normalized $rSO_2$ value, original $rSO_2$ value corresponding to the normalized $rSO_2$ value, a plot of COx versus MAP, and/or an $rSO_2$—$SpO_2$ curve. In certain embodiments, the controller 18 may generate an alarm signal indicative of the patient's autoregulation status (e.g., indicating autoregulation is not intact) and provide the alarm signal to the output device 20.

Figure 4:
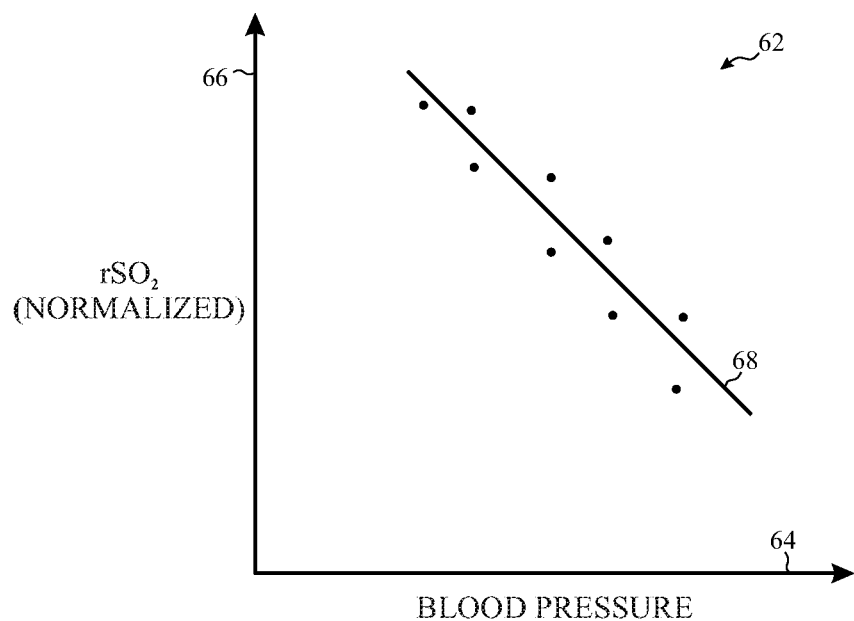
FIG. 4 is an example of a graph illustrating a linear correlation between normalized oxygen saturation values and blood pressure values.

FIG. 4 is an example of a graph 62 illustrating a linear correlation between blood pressure measurements 64 (e.g., arterial blood pressure measurements) and normalized regional oxygen saturation measurements 66. The result of the linear correlation may be a regression line 68 between the blood pressure measurements 64 and the normalized regional oxygen saturation measurements 66, and the slope of the regression line 68 may be indicative of the patient's autoregulation status. In the illustrated example, the slope of the regression line 68 is negative and, thus, the COx value is between −1 and 0, which as discussed above, may indicate proper autoregulation. In such cases, the controller 18 may determine that the patient's cerebral autoregulation is functioning properly and may generate and/or output an appropriate signal indicative of the patient's autoregulation status to the output device 20, for example. However, when the regression line 68 has a positive slope and the COx value is between 0 and 1 or above some predetermined threshold (e.g., 0.1, 0.2, 0.3, 0.4, 0.5, 0.6, 0.7, 0.8, or 0.9, as discussed above), the controller 18 may determine that the patient's autoregulation is impaired and may generate and/or output the appropriate signal indicative of the patient's autoregulation status. In some instances, the signal indicative of the patient's autoregulation status may be displayed as a graph similar to the graph 62 of FIG. 4 shown on the output device 20 for presentation to a treating physician.

Figure 5:
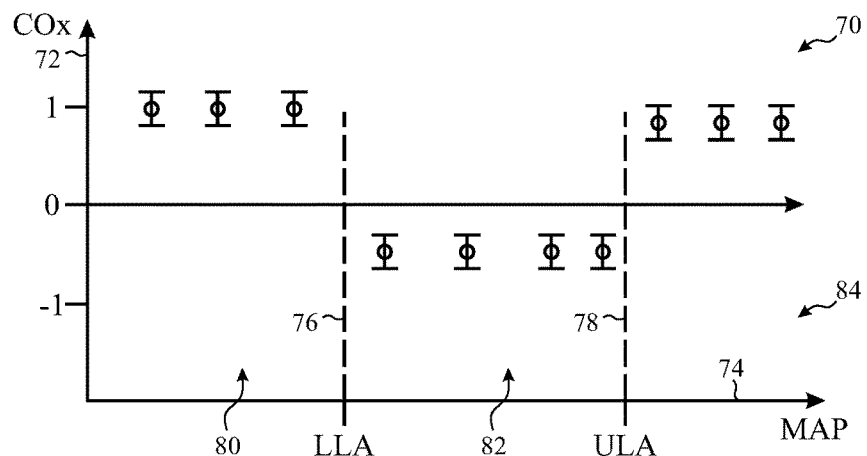
FIG. 5 is an example of a graph illustrating cerebral oximetry index (COx) plotted against mean arterial pressure (MAP)

FIG. 5 is an example of a graph 70 illustrating COx 72 plotted against blood pressure 74 (e.g., MAP). In the graph, individual data points (e.g., derived utilizing normalized regional oxygen saturation values) are binned according to the blood pressure 74. As shown, the data points are distributed (e.g., spread) across COx values 72 in a characteristic manner at the various blood pressures 74. The data points may be utilized to determine the LLA 76 and/or the ULA 78 to determine a lower impaired autoregulation zone 80, an intact autoregulation zone 82, and a higher impaired autoregulation zone 84. The data points may generally vary between −1 and +1 at the intermediate blood pressures associated with the intact autoregulation zone 82, and may cluster at approximately +1 at the lower blood pressures associated with the lower impaired autoregulation zone 80 and at the higher blood pressures associated with the higher impaired autoregulation zone 84. In some instances, the signal indicative of the patient's autoregulation status may be displayed as a graph similar to the graph 70 of FIG. 5 shown on the output device 20 for presentation to a treating physician.

Figure 6:
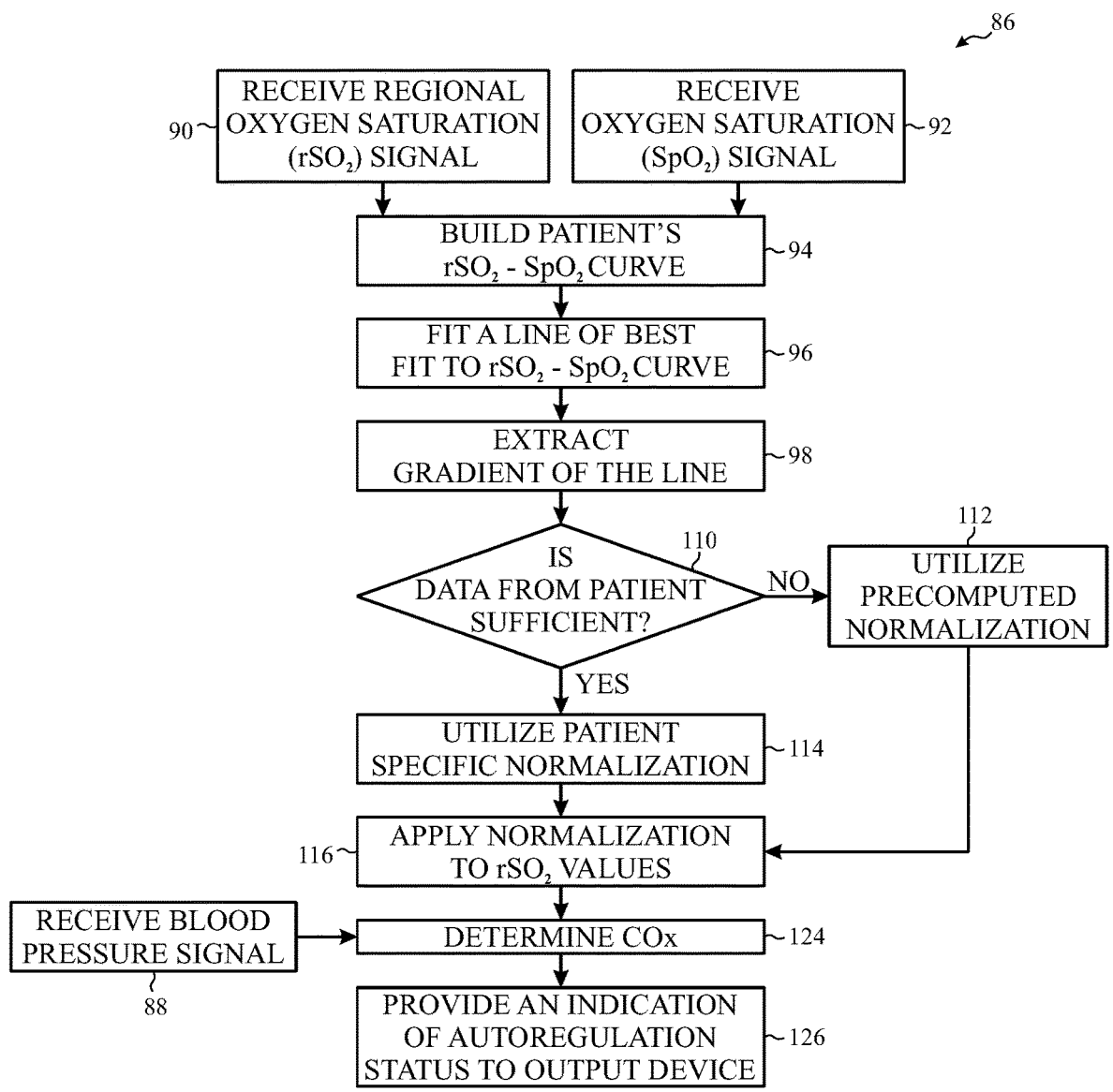
FIG. 6 is a process flow diagram of a method of monitoring autoregulation that includes determining what data to utilize in normalizing a regional oxygen saturation signal, in accordance with an embodiment.

As mentioned above, in certain embodiments, the relationship between regional oxygen saturation and oxygen saturation for normalization of the regional oxygen saturation signal may be from patient derived data (e.g., a gradient of a best fit line of an $rSO_2$—$SpO_2$ curve generated from the regional oxygen saturation signal and the oxygen saturation signal). In addition, as mentioned above, in certain embodiments, the controller 18 may initially rely on the historical data in determining the relationship and, subsequently, switch to utilizing patient's data upon collecting sufficient patient data (i.e., enough data to calculate a reliable normalization gradient). FIG. 6 is a process flow diagram of a method 86 of monitoring autoregulation that includes determining what data to utilize in normalizing a regional oxygen saturation signal, in accordance with an embodiment. Some or all of the steps of the method 86 may be implemented by the controller 18 (e.g., the processor 30 of the controller 18) of FIG. 1. In step 88, the controller 18 may receive the blood pressure signal (e.g., arterial blood pressure signal) from the blood pressure sensor 12, as set forth above. In step 90, the controller 18 may receive the regional oxygen saturation signal (e.g., from the regional oxygen saturation sensor 14, as set forth above). In step 92, the controller 18 may receive the oxygen saturation signal (e.g., from the oxygen saturation sensor 16, as set forth above). Steps 88, 90, and 92 may occur simultaneously.

Figure 7:
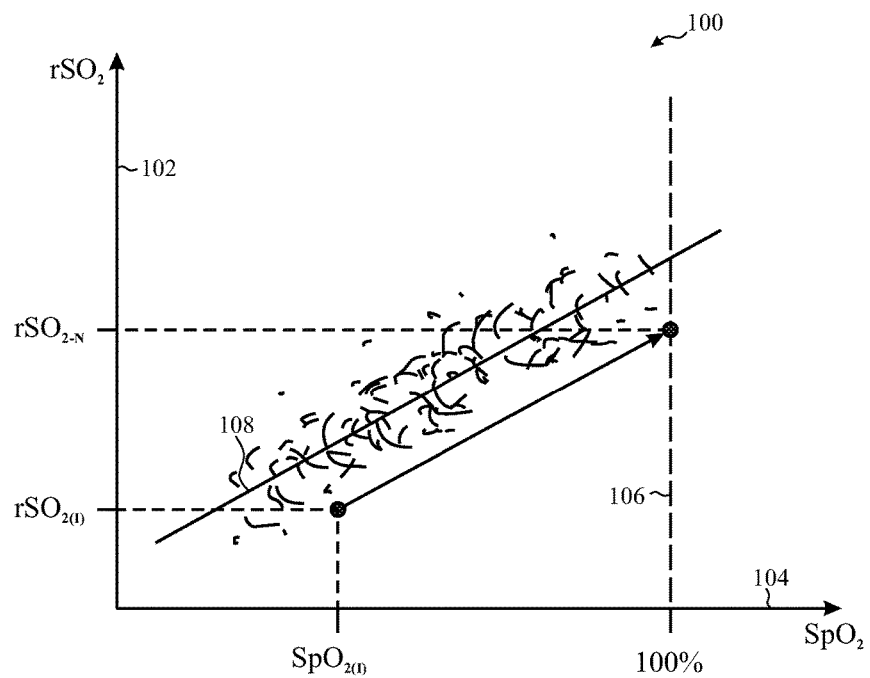
FIG. 7 is an example of an $rSO_2$—$SpO_2$ curve utilized to derive a gradient for normalization of a regional oxygen saturation signal.

In step 94, the controller 18 may generate or build an $rSO_2$—$SpO_2$ curve based on the data from the regional oxygen saturation signal and the oxygen saturation signal. In step 96, the controller 18 may fit a line of best fit to the data. The line of best fit may be determined through least squares, least median squares, or other techniques. In step 98, the controller 18 may extract a gradient (e.g., slope) of the line that may be utilized as m in Eq. 1 above for normalizing the regional oxygen saturation signal. FIG. 7 is an example of an $rSO_2$—$SpO_2$ curve 100 derived from plotting $rSO_2$ 102 and $SpO_2$ 104 data from the regional oxygen saturation signal and the oxygen saturation signal, respectively. The vertical line 106 marks the 100% $SpO_2$ level. Line 108 represents the line of best fit fitted to the data. The gradient or slope of line 108 may be utilized as m in Eq. 1 above for normalizing the regional oxygen saturation signal. Utilizing the gradient of line 108 as m in Eq. 1 and the currently acquired values, $rSO_2$ (i) and $SpO_2$ (i), the $rSO_2$—N may be obtained that corresponds to a $SpO_2$ that equals 100%.

Figure 8:
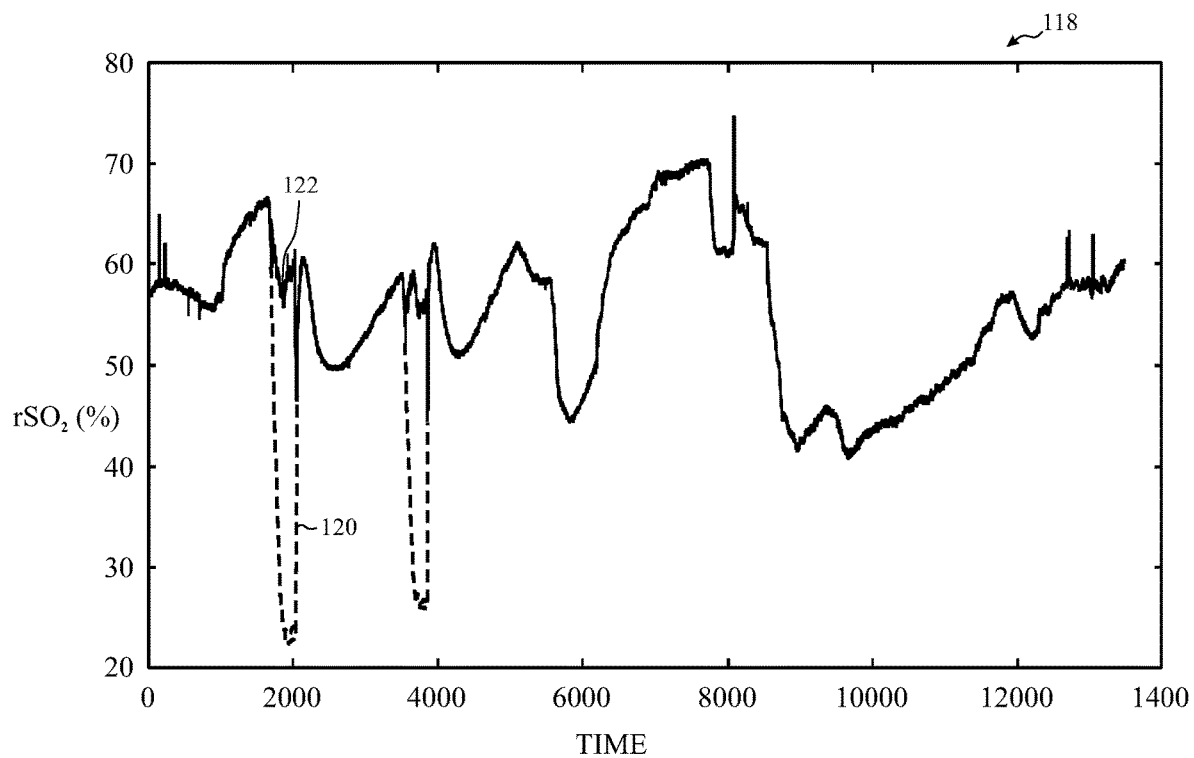
FIG. 8 is an example of a graph illustrating a regional oxygen saturation signal before and after normalization.

Returning to FIG. 6, in step 110, the controller 18 may determine whether the data collected from the patient (e.g., via the regional oxygen saturation signal and oxygen saturation signal) is sufficient to calculate a reliable normalization gradient. Step 110 may occur prior to, concurrent with, and/or subsequent to one or more of steps 94, 96, and 98. If the data is not sufficient, in step 112, the controller 18 may determine to utilize a precomputed normalization (i.e., utilizing historical data or assuming m=1) as described above in normalizing the regional oxygen saturation signal. If the data is sufficient, in step 114, the controller 18 may determine to utilize the gradient derived from the $rSO_2$—$SpO_2$ curve as described above in normalizing the regional oxygen saturation signal. Thus, in certain embodiments, the controller 18 may initially utilize the precomputed normalization and then switch to utilizing the gradient derived from the $rSO_2$—$SpO_2$ curve once the data is sufficient. In step 116, the controller 18 may apply normalization to the regional oxygen saturation signal (e.g., utilizing Eq. 1). FIG. 8 is an example of a graph 118 illustrating a regional oxygen saturation signal before (signal 120) and after normalization (normalized signal 122).

Returning to FIG. 6, in step 124, the controller 18 may determine the autoregulation status of the patient (e.g., COx) based on the linear correlation between blood pressure measurements of the blood pressure signal and the normalized regional oxygen saturation signal. In certain embodiments, the controller 18 may further determine the autoregulation status of the patient by plotting the COx value against the MAP (as well as determine the LLA and/or ULA) and determining whether the patient's autoregulation is intact or not (i.e., is the current blood pressure within an intact autoregulation zone). In step 126, the controller 18 may output the COx or a signal indicative of the patient's autoregulation status to the output device 20. In such cases, the controller 18 may cause the output device 20 to present a visual or audible indication of the COx value or the patient's autoregulation status. Also, the controller 18 may cause the output device 20 to provide a visual or audible indication of the normalized $rSO_2$ value, original $rSO_2$ value corresponding to the normalized $rSO_2$ value, a plot of COx versus MAP, and/or an $rSO_2$—$SpO_2$ curve. In certain embodiments, the controller 18 may generate an alarm signal indicative of the patient's autoregulation status (e.g., indicating autoregulation is not intact) and provide the alarm signal to the output device 20.

Figure 9:
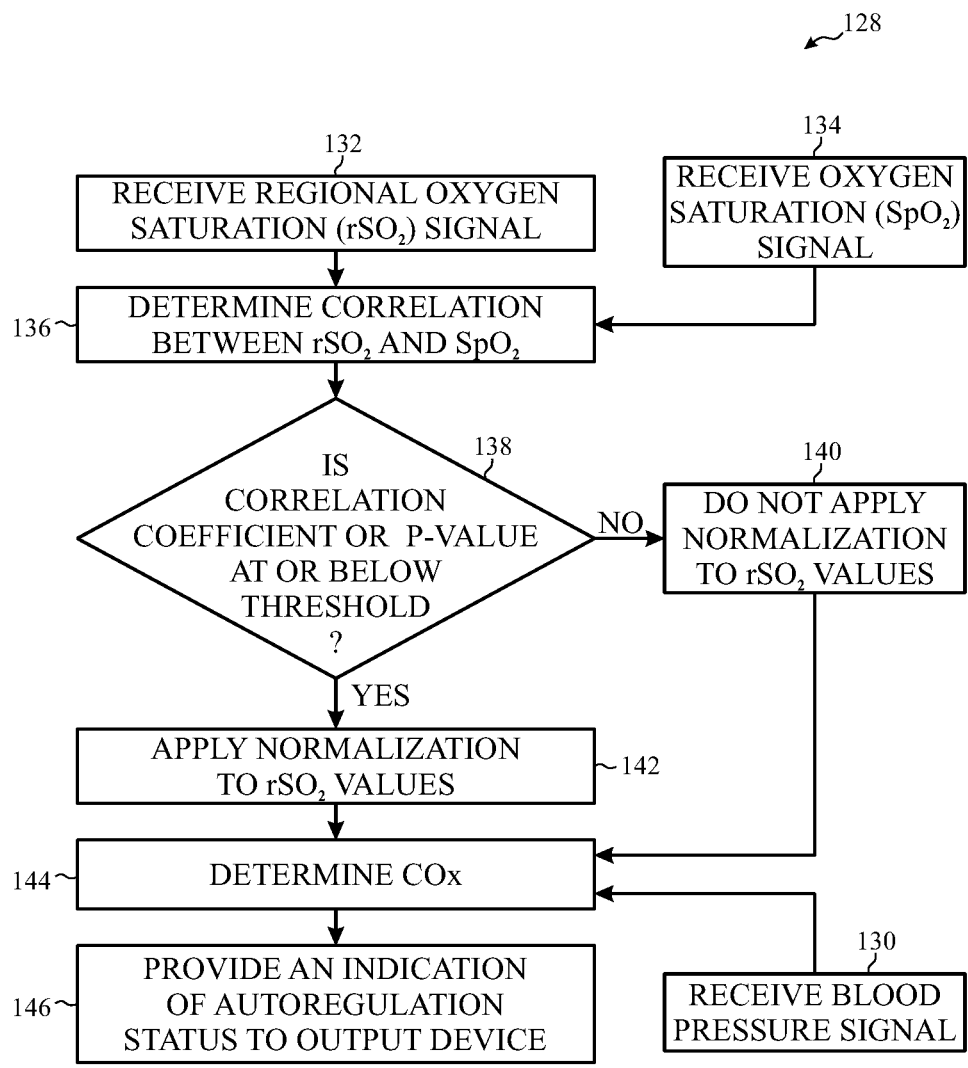
FIG. 9 is a process flow diagram of a method of monitoring autoregulation that includes determining whether to apply normalization to the regional oxygen saturation signal (e.g., based on a strength of correlation), in accordance with an embodiment.

As mentioned above, in certain embodiments, the controller 18 may only apply normalization to the regional oxygen saturation signal only if there is only a strong correlation between the regional oxygen saturation signal and the oxygen saturation signal. FIG. 9 is a process flow diagram of a method 128 of monitoring autoregulation that includes determining if normalization should be applied to the regional oxygen saturation signal, in accordance with an embodiment. Some or all of the steps of the method 128 may be implemented by the controller 18 (e.g., the processor 30 of the controller 18) of FIG. 1. In step 130, the controller 18 may receive the blood pressure signal (e.g., arterial blood pressure signal) from the blood pressure sensor 12, as set forth above. In step 132, the controller 18 may receive the regional oxygen saturation signal (e.g., from the regional oxygen saturation sensor 14, as set forth above). In step 134, the controller 18 may receive the oxygen saturation signal (e.g., from the oxygen saturation sensor 16, as set forth above). Steps 130, 132, and 134 may occur simultaneously.

In step 136, the controller 18 may determine a correlation between the regional oxygen saturation signal and the oxygen saturation signal. Determining a correlation may include determining a linear correlation between the regional oxygen saturation signal and the oxygen saturation signal. In certain embodiments, a quality metric for correlation such as a correlation coefficient (e.g., based on a Pearson coefficient) and/or a significance value (e.g., a p-value) associated with the linear correlation of the regional oxygen saturation signal and the oxygen saturation signal may be determined. In step 138, the controller 18 may compare the quality metric for correlation to a threshold value (e.g., desired correlation coefficient value or significance level). If the quality metric is at or below the threshold value, in step 140, the controller 18 may decide to not apply normalization to the regional oxygen saturation signal. If the quality metric is above the threshold value, in step 142, the controller 18 may decide to apply normalization to the regional oxygen saturation signal (e.g., utilizing Eq. 1) as described above.

In step 144, the controller 18 may determine the autoregulation status of the patient (e.g., COx) based on the linear correlation between blood pressure measurements of the blood pressure signal and the regional oxygen saturation signal (if normalization was not applied) or the normalized regional oxygen saturation signal (if normalization was applied). In certain embodiments, the controller 18 may further determine the autoregulation status of the patient by plotting the COx value against the MAP (as well as determine the LLA and/or ULA) and determining whether the patient's autoregulation is intact or not (i.e., is the current blood pressure within an intact autoregulation zone). In step 146, the controller 18 may output the COx or a signal indicative of the patient's autoregulation status to the output device 20. In such cases, the controller 18 may cause the output device 20 to present a visual or audible indication of the COx value or the patient's autoregulation status. Also, the controller 18 may cause the output device 20 to provide a visual or audible indication of the normalized $rSO_2$ value, original $rSO_2$ value corresponding to the normalized $rSO_2$ value, a plot of COx versus MAP, and/or an $rSO_2$—$SpO_2$ curve. In certain embodiments, the controller 18 may generate an alarm signal indicative of the patient's autoregulation status (e.g., indicating autoregulation is not intact) and provide the alarm signal to the output device 20.

Figure 10:
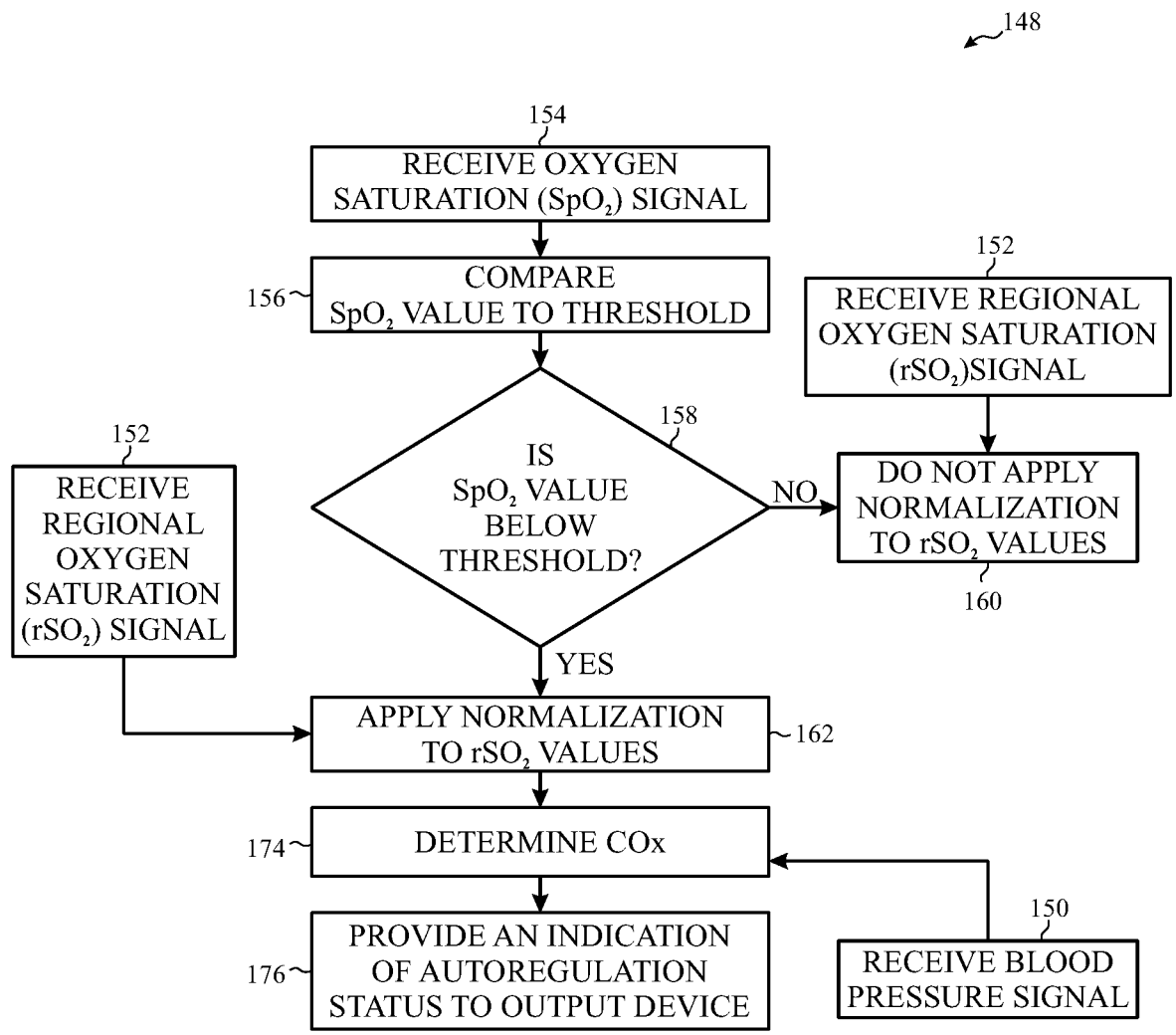
FIG. 10 is a process flow diagram of a method of monitoring autoregulation that includes determining whether to apply normalization to the regional oxygen saturation signal (e.g., based on the oxygen saturation level), in accordance with an embodiment.

As mentioned above, in certain embodiments, the controller 18 may only apply normalization to the regional oxygen saturation signal if the SpO$_2$ falls below a particular threshold (e.g., 95% SpO$_2$). FIG. 10 is a process flow diagram of a method 148 of monitoring autoregulation that includes determining to apply normalization to the regional oxygen saturation signal only if the oxygen saturation signal falls below a threshold, in accordance with an embodiment. Some or all of the steps of the method 148 may be implemented by the controller 18 (e.g., the processor 30 of the controller 18) of FIG. 1. In step 150, the controller 18 may receive the blood pressure signal (e.g., arterial blood pressure signal) from the blood pressure sensor 12, as set forth above. In step 152, the controller 18 may receive the regional oxygen saturation signal (e.g., from the regional oxygen saturation sensor 14, as set forth above). In step 154, the controller 18 may receive the oxygen saturation signal (e.g., from the oxygen saturation sensor 16, as set forth above). Steps 150, 152, and 154 may occur simultaneously.

Figure 11:
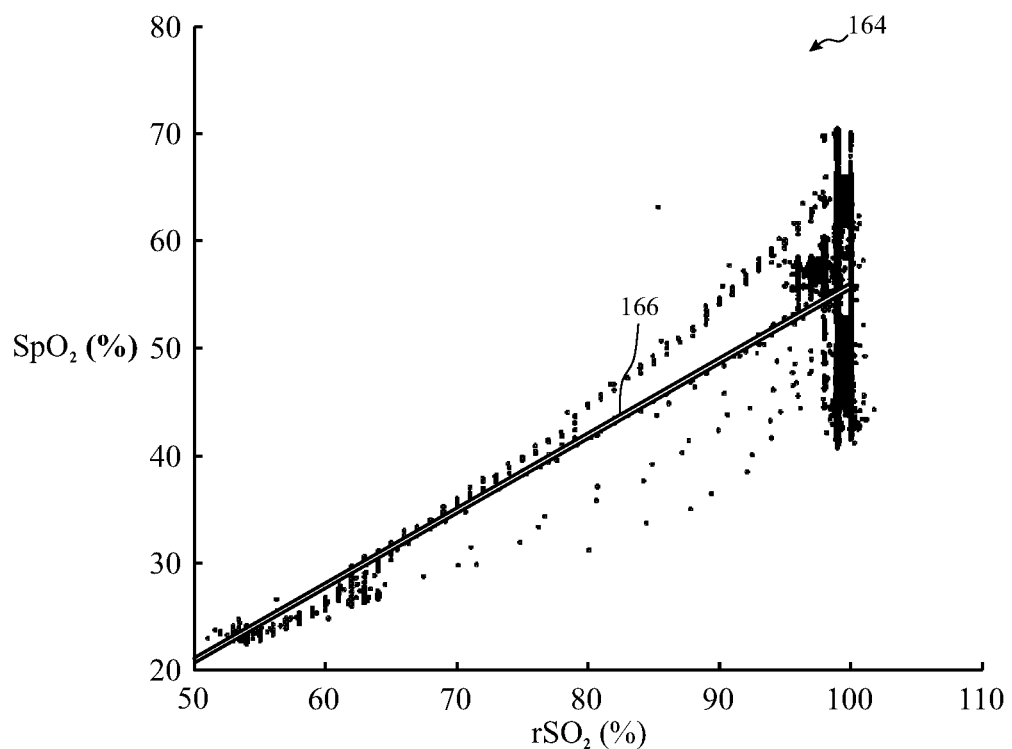
FIG. 11 is an example of an $rSO_2$—$SpO_2$ curve having a least squares regression line fitted to all of the data.
Figure 12:
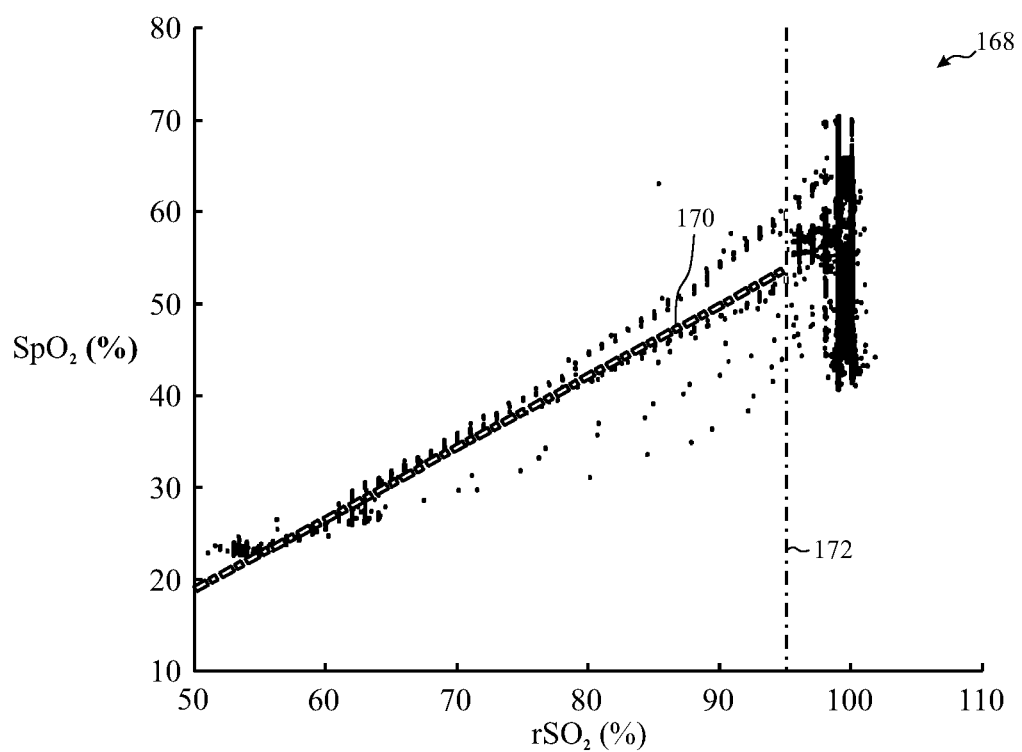
FIG. 12 is an example of an $rSO_2$—$SO_2$ curve having a least squares regression line fitted to a portion of the data.

In step 158, the controller 18 may determine if the SpO$_2$ value (derived from the oxygen saturation signal) falls below an oxygen saturation threshold. For example, the oxygen saturation threshold could range from 90% to 99%. In certain embodiments, the oxygen saturation threshold may be 95%. If the SpO$_2$ value falls below the oxygen saturation threshold, in step 160, the controller 18 may decide to apply normalization (e.g., selectively) to the regional oxygen saturation signal (e.g., only with regard to rSO$_2$ data corresponding to SpO$_2$ values falling below the oxygen saturation threshold). If the SpO$_2$ value equals or exceeds the oxygen saturation threshold, in step 162, the controller 18 may decide not to apply normalization to the regional oxygen saturation signal. In particular, in normalizing the regional oxygen saturation signal, the controller 18 may utilize the following equation:

$$rSO_2\text{—}N = rSO_2(i) + m_{95} \times (95 - SpO_2(i)), \text{ for } SpO_2(i) < 95\% \quad (2)$$

wherein rSO$_2$—N represents the normalized rSO$_2$ value, rSO2 (i) represents the currently acquired rSO$_2$ (i) value, SpO$_2$ (i) represents the currently acquired SpO$_2$ value, and m$_{95}$ represents a numerical representation of the relationship between regional oxygen saturation and oxygen saturation ranging between 0 to 1 for the data (oxygen saturation data and corresponding regional oxygen saturation data) associated with SpO$_2$ values less than the oxygen saturation threshold. Eq. 2 is an example of the normalization equation when the oxygen threshold value equals 95% and may be altered to the desired oxygen threshold value (e.g., between 90% and 99%). FIG. 11 provides an example of an rSO$_2$—SpO$_2$ curve 164 having a least squares regression line 166 fitted to all of the data (e.g., up to 100% SpO$_2$). FIG. 12 provides an example of an rSO$_2$—SpO$_2$ curve 168 having a least squares regression line 170 fitted to some of the data (e.g., corresponding to less 95% SpO$_2$, which is represented by vertical line 172).

Returning to FIG. 10, in step 174, the controller 18 may determine the autoregulation status of the patient (e.g., COx) based on the linear correlation between blood pressure measurements of the blood pressure signal and the regional oxygen saturation signal (for the portion of the signal corresponding to SpO$_2$ values at or above the oxygen saturation threshold) and the normalized regional oxygen saturation signal (for the portion of the signal corresponding to SpO$_2$ values below the oxygen saturation threshold). In certain embodiments, the controller 18 may further determine the autoregulation status of the patient by plotting the COx value against the MAP (as well as determine the LLA and/or ULA) and determining whether the patient's autoregulation is intact or not (i.e., is the current blood pressure within an intact autoregulation zone). In step 176, the controller 18 may output the COx or a signal indicative of the patient's autoregulation status to the output device 20. In such cases, the controller 18 may cause the output device 20 to present a visual or audible indication of the COx value or the patient's autoregulation status. Also, the controller 18 may cause the output device 20 to provide a visual or audible indication of the normalized rSO$_2$ value, original rSO$_2$ value corresponding to the normalized rSO$_2$ value, a plot of COx versus MAP, and/or an rSO$_2$—SpO$_2$ curve. In certain embodiments, the controller 18 may generate an alarm signal indicative of the patient's autoregulation status (e.g., indicating autoregulation is not intact) and provide the alarm signal to the output device 20.

Figure 13:
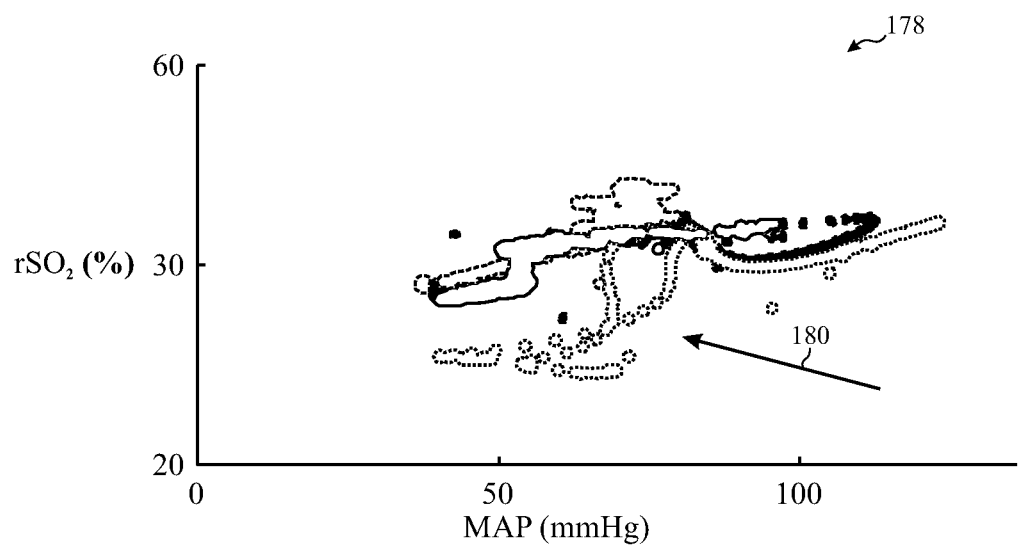
FIG. 13 is an example of a graph illustrating $rSO_2$ plotted against MAP.
Figure 14:
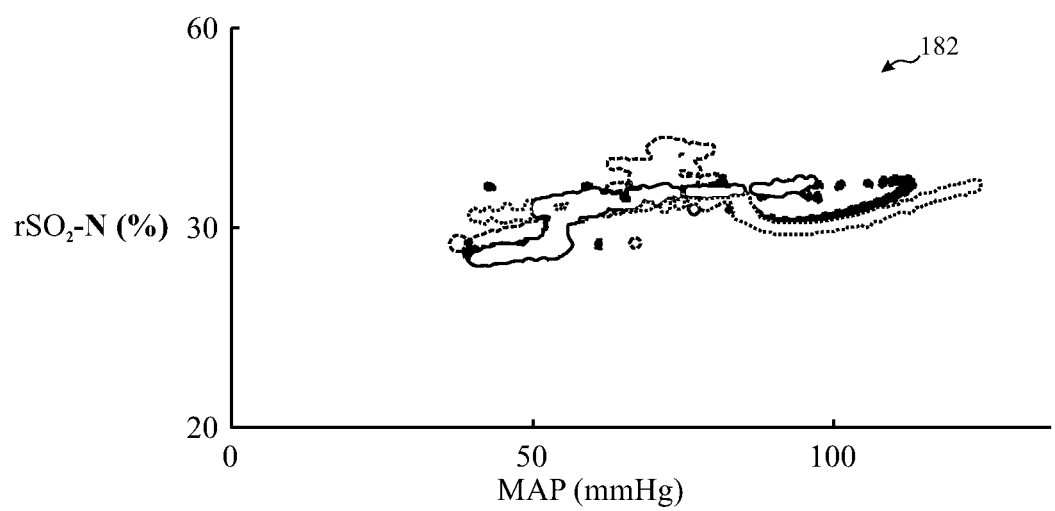
FIG. 14 is an example of a graph illustrating normalized $rSO_2$ (rSO2-N) plotted against MAP.

As noted above, normalization may enable correcting the regional oxygen saturation signal for changes in the oxygen saturation signal. FIG. 13 is an example of a graph 178 illustrating rSO$_2$ plotted against MAP. Arrow 180 points to a region (e.g., spur) where some of the rSO$_2$ values have fallen to a lower level (e.g., relative to the other rSO$_2$ values) due to SpO$_2$ induced variations. FIG. 13 is an example of a graph 182 illustrating normalized rSO$_2$ (rSO$_2$—N, determined utilizing the techniques described above) plotted against MAP. As depicted in the graph 182 of FIG. 14, the spur or region where some of the rSO$_2$ values have fallen to a lower level in FIG. 13 has been corrected. Normalization of the regional oxygen saturation signal may enable more accurate autoregulation information to be presented to a medical professional.

Figure 15:
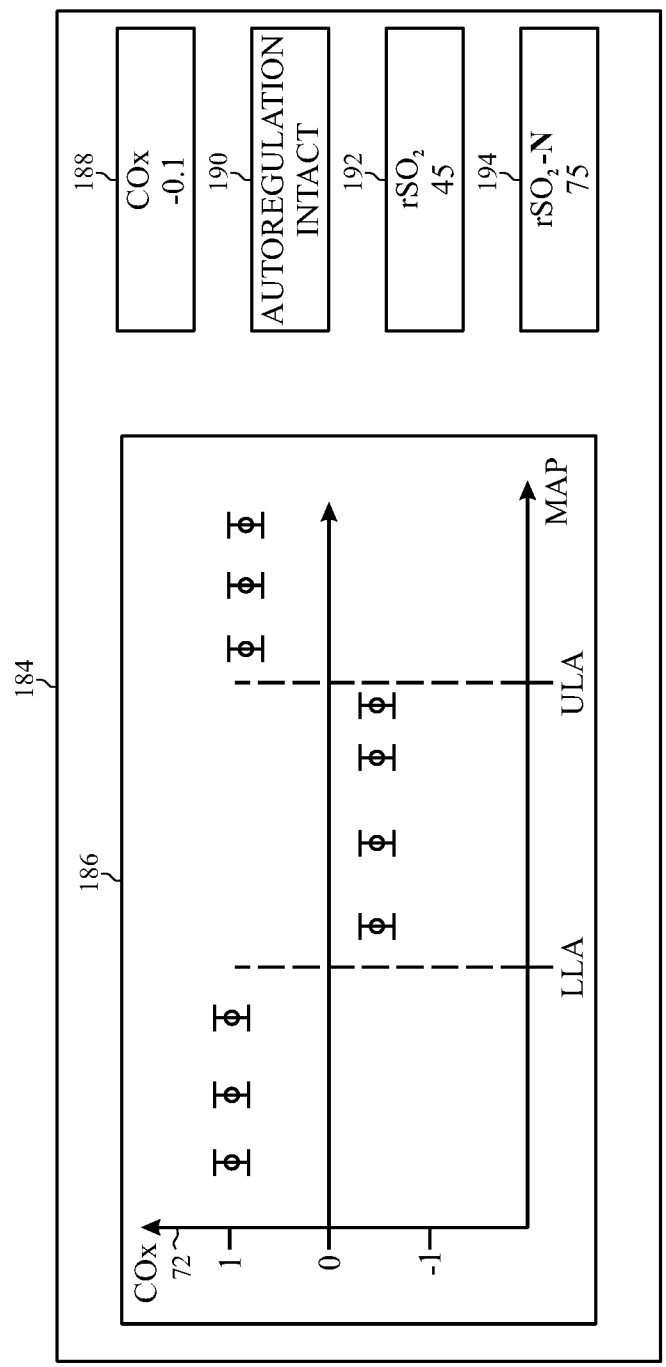
FIG. 15 is an embodiment of a display configured to display various information related to an autoregulation status of a patient.

FIG. 15 is an embodiment of a display 184 of the output device 20 that is configured to display various information related to an autoregulation status of a patient. As shown, the display 184 may be configured to provide a representation 186 of COx plotted against MAP such as shown in FIG. 5. In certain embodiments, the display 184 may be configured to provide a representation of the regional oxygen saturation signal (e.g., prior to and/or after normalization), a representation of the blood pressure signal, and/or a representation of the COx signal. In some embodiments, the display 184 may provide a representation of any of the other graphs or curves discussed above (e.g., rSO$_2$—SpO$_2$ curves, rSO$_2$-MAP plots, etc.). As shown, the display 184 may also be configured to provide a COx value 188 (current COx value or average COx value), which may be updated continuously or at predetermined intervals. Also, as shown, the display 184 may be configured to provide an indication of the patient's autoregulation status 190 (intact or impaired). Further, as shown, the display may be configured to provide the current normalized rSO$_2$ value 192 (rSO$_2$—N) and the corresponding rSO$_2$ value 194 prior to normalization.

Oxygen saturation measured at the finger may have substantial time delays (e.g., over one minute or longer) in recording changes in saturation when compared to regional oxygen saturation measured at the forehead. As noted above, in certain embodiments, the controller 18 may compensate for this time delay in normalizing the regional oxygen saturation signal. In particular, in normalizing the regional oxygen saturation signal, the controller 18 may utilize the following equation:

$$rSO_2\text{—}N = rSO_2(i-T) + m \times (100 - SpO_2(i)), \quad (3)$$

wherein rSO$_2$—N represents the normalized rSO$_2$ value, SpO$_2$ (i) represents the currently acquired SpO$_2$ value, rSO2 (i–T) represents the acquired rSO$_2$ (i) value at a time T (representing the lag time at the finger site for measuring the SpO$_2$ (i)), and m represents a numerical representation of the relationship between regional oxygen saturation and oxygen saturation ranging between 0 and 1. For example, if the lag time, T, is one minute, the $rSO_2$ value corresponding to the $SpO_2$ (i) to be utilized for normalization would be the $rSO_2$ value measured one minute earlier.

Typically, the $SpO_2$ values presented to an end user (e.g., healthcare professional) are truncated or (capped) by manufacturers at 100%. These truncated $SpO_2$ values may be utilized in the techniques discussed above to normalize the $rSO_2$ values. However, in certain embodiments, the uncapped $SpO_2$ values (i.e., including those values extending above 100% at their calculated value rather than their capped value) may be utilized in the techniques discussed above to generate $rSO_2$-N.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims. Further, it should be understood that certain elements of the disclosed embodiments may be combined or exchanged with one another.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

What is claimed is:

1. A method for monitoring autoregulation, comprising:
   receiving, by one or more processors, a blood pressure signal indicative of a blood pressure of a patient, an oxygen saturation signal indicative of an oxygen saturation of the patient, and a regional oxygen saturation signal indicative of a regional oxygen saturation of the patient;
   determining, by the one or more processors, a gradient of a best fit line for a curve generated based on oxygen saturation data and regional oxygen saturation data;
   normalizing, by the one or more processors, the regional oxygen saturation signal using the gradient of the best fit line to correct for variation in the regional oxygen saturation signal due to changes in the oxygen saturation signal;
   determining, by the one or more processors, a linear correlation between the blood pressure signal and the normalized regional oxygen saturation signal;
   determining, by the one or more processors, a value indicative of an autoregulation status of the patient based on the linear correlation; and
   at least one of:
   presenting, via a display, information indicative of the autoregulation status of the patient; or
   outputting, via an audio device, information indicative of the autoregulation status of the patient,
   wherein the information indicative of the autoregulation status of the patient is based on the value indicative of the autoregulation status of the patient.

2. The method of claim 1, further comprising providing a cerebral oximetry index value to at least one of the display or the audio device.

3. The method of claim 1, further comprising providing a normalized regional oxygen saturation value derived from the normalized regional oxygen saturation signal to at least one of the display or the audio device.

4. The method of claim 3, further comprising providing a regional oxygen saturation value derived from the regional oxygen saturation signal and corresponding to the normalized regional oxygen saturation value to at least one of the display or the audio device.

5. The method of claim 1, wherein the oxygen saturation data and the regional oxygen saturation data are based on historical data from the patient or from other subjects.

6. The method of claim 1, wherein normalizing the regional oxygen saturation signal comprises compensating for a time delay in receiving the oxygen saturation signal.

7. The method of claim 5, further comprising determining an amount of data gathered from the oxygen saturation signal and the regional oxygen saturation signal is insufficient to calculate a reliable normalization gradient based on the oxygen saturation signal and the regional oxygen saturation signal, wherein normalizing the regional oxygen saturation signal comprises normalizing the regional oxygen saturation signal based on the historical data in response to determining that the amount of data gathered is insufficient to calculate a reliable normalization gradient based on the oxygen saturation signal and the regional oxygen saturation signal.

8. The method of claim 1, wherein normalizing the regional oxygen saturation signal, comprises using the equation: $rSO_2-N=rSO_2(i)+m\times(100-SpO_2(i))$, wherein $rSO_2-N$ represents a normalized regional oxygen saturation value, wherein $rSO_2(i)$ represents an acquired regional oxygen saturation value, wherein $SpO_2(i)$ represents an acquired blood oxygen saturation value, and wherein m represents a numerical representation of the relationship between regional oxygen saturation and oxygen saturation ranging between 0 and 1.

9. The method of claim 1, wherein the oxygen saturation data is based on the oxygen saturation signal and the regional oxygen saturation data is based on the regional oxygen saturation signal.

10. The method of claim 9, further comprising determining an amount of data gathered from the oxygen saturation signal and the regional oxygen saturation signal is sufficient to determine a reliable normalization gradient based on the oxygen saturation signal and the regional oxygen saturation signal, wherein normalizing the regional oxygen saturation signal comprises normalizing the regional oxygen saturation signal in response to determining that the amount of data gathered is sufficient to determine the reliable normalization gradient based on the oxygen saturation signal and the regional oxygen saturation signal.

11. A monitor for monitoring autoregulation, the monitor comprising:
   an output device comprising at least one of a display or an audio device; and
   one or more processors configured to:
   receive a blood pressure signal indicative of a blood pressure of a patient, an oxygen saturation signal indicative of an oxygen saturation of the patient, and a regional oxygen saturation signal indicative of a regional oxygen saturation of the patient;
determine a gradient of a best fit line for a curve generated based on oxygen saturation data and regional oxygen saturation data;
normalize the regional oxygen saturation signal using the gradient of the best fit line to correct for variation in the regional oxygen saturation signal due to changes in the oxygen saturation signal;
determine a linear correlation between the blood pressure signal and the normalized regional oxygen saturation signal;
determine a value indicative of an autoregulation status of the patient based on the linear correlation; and
at least one of:
presenting, via a display, information indicative of the autoregulation status of the patient; or
outputting, via an audio device, information indicative of the autoregulation status of the patient,
wherein the information indicative of the autoregulation status of the patient is based on the value indicative of the autoregulation status of the patient.

12. The monitor of claim 11, wherein the oxygen saturation data and the regional oxygen saturation data are based on historical data from the patient or from other subjects.

13. The monitor of claim 11, wherein the one or more processors are configured to normalize the regional oxygen saturation signal using the equation: $rSO_2\text{—}N=rSO_2(i)+m\times(100-SpO_2(i))$, wherein $rSO_2\text{—}N$ represents a normalized regional oxygen saturation value, wherein $rSO_2(i)$ represents an acquired regional oxygen saturation value, wherein $SpO_2(i)$ represents an acquired blood oxygen saturation value, and wherein m represents a numerical representation of the relationship between regional oxygen saturation and oxygen saturation ranging between 0 and 1.

14. The monitor of claim 11, wherein the oxygen saturation data is based on the oxygen saturation signal and the regional oxygen saturation data is based on the regional oxygen saturation signal.

15. A system for monitoring autoregulation, the system comprising:
an oxygen saturation sensor configured to obtain an oxygen saturation signal indicative of an oxygen saturation of a patient;
a regional oxygen saturation sensor configured to obtain a regional oxygen saturation signal indicative of a regional oxygen saturation of the patient;
an output device comprising at least one of a display or an audio device; and
a controller comprising one or more processors configured to:
receive a blood pressure signal indicative of a blood pressure of the patient, the oxygen saturation signal, and the regional oxygen saturation signal;
determine a gradient of a best fit line for a curve generated based on oxygen saturation data and regional oxygen saturation data;
normalize the regional oxygen saturation signal using the gradient of the best fit line to correct for variation in the regional oxygen saturation signal due to changes in the oxygen saturation signal;
determine a linear correlation between the blood pressure signal and the normalized regional oxygen saturation signal;
determine a value indicative of an autoregulation status of the patient based on the linear correlation; and
at least one of:
presenting, via a display, information indicative of the autoregulation status of the patient; or
outputting, via an audio device, information indicative of the autoregulation status of the patient,
wherein the information indicative of the autoregulation status of the patient is based on the value indicative of the autoregulation status of the patient.

16. The system of claim 15, wherein the controller is configured to cause the output device to present, via the display, or output, via the audio device, a cerebral index value indicative of the autoregulation status of the patient, a normalized regional oxygen saturation value derived from the normalized regional oxygen saturation signal, a regional oxygen saturation value derived from the regional oxygen saturation signal and corresponding to the normalized regional oxygen saturation value, or any combination thereof.

17. The method of claim 1, further comprising determining a quality metric of a correlation between the oxygen saturation signal and the regional oxygen saturation is above a threshold value, wherein normalizing the regional oxygen saturation signal comprises normalizing the regional oxygen saturation signal in response to determining that the quality metric is above the threshold value.

18. The method of claim 1, further comprising determining an oxygen saturation value derived from the oxygen saturation signal is below an oxygen saturation threshold value, and wherein normalizing the regional oxygen saturation signal comprises normalizing the regional oxygen saturation signal in response to determining that the oxygen saturation value is below the oxygen saturation threshold value.

19. The monitor of claim 11, wherein the one or more processors are configured to determine a quality metric of a correlation between the oxygen saturation signal and the regional oxygen saturation is above a threshold value, and normalize the regional oxygen saturation signal in response to determining the quality metric is above the threshold value.

20. The monitor of claim 11, wherein the one or more processors are configured to determine an oxygen saturation value derived from the oxygen saturation signal is below an oxygen saturation threshold value and normalize the regional oxygen saturation signal in response to determining the oxygen saturation value is below the oxygen saturation threshold value.

* * * * *